(12) United States Patent
Wollmann et al.

(10) Patent No.: US 8,003,636 B2
(45) Date of Patent: Aug. 23, 2011

(54) CERTAIN CRYSTALLINE DIPHENYLAZETIDINONE HYDRATES, PHARMACEUTICAL COMPOSITIONS THEREOF AND METHODS FOR THEIR USE

(75) Inventors: Theodor Andreas Wollmann, Hattersheim (DE); Regina Duffy, Hattersheim (DE); Frank Cullmann, Eschborn (DE)

(73) Assignee: Sanofi-Aventis Deutschland GmbH (DE)

( * ) Notice: Subject to any disclaimer, the term of this patent is extended or adjusted under 35 U.S.C. 154(b) by 350 days.

(21) Appl. No.: 12/269,802

(22) Filed: Nov. 12, 2008

(65) Prior Publication Data

US 2009/0203578 A1  Aug. 13, 2009

Related U.S. Application Data

(60) Provisional application No. 60/990,225, filed on Nov. 26, 2007.

(30) Foreign Application Priority Data

Nov. 13, 2007 (DE) .......... 10 2007 054 497

(51) Int. Cl.
C07D 205/08 (2006.01)
A61K 31/397 (2006.01)
(52) U.S. Cl. .................. 514/210.02; 540/200
(58) Field of Classification Search .......... 540/200; 514/210.02

See application file for complete search history.

(56) References Cited

U.S. PATENT DOCUMENTS

| | | | |
|---|---|---|---|
| 4,596,789 A | 6/1986 | Dutta et al. |
| 5,190,923 A | 3/1993 | Vincent et al. |
| 5,656,624 A | 8/1997 | Vaccaro et al. |
| 5,756,470 A | 5/1998 | Yumibe et al. |
| 5,846,966 A | 12/1998 | Rosenblum et al. |
| 5,889,002 A | 3/1999 | Nielsen et al. |
| 6,221,633 B1 | 4/2001 | Ertl et al. |
| 6,221,897 B1 | 4/2001 | Frick et al. |
| 6,225,310 B1 | 5/2001 | Nielsen et al. |
| 6,245,744 B1 | 6/2001 | Frick et al. |
| 6,268,343 B1 | 7/2001 | Knudsen et al. |
| 6,342,512 B1 | 1/2002 | Kirsch et al. |
| 6,380,230 B1 | 4/2002 | Brodin et al. |
| 6,498,156 B2 | 12/2002 | Glombik et al. |
| 6,525,083 B2 | 2/2003 | Acton, III et al. |
| 6,589,984 B1 | 7/2003 | Naniwa et al. |
| 6,624,185 B2 | 9/2003 | Glombik et al. |
| 6,861,444 B2 | 3/2005 | Ikuta et al. |
| 6,884,812 B2 | 4/2005 | Glombik et al. |
| 6,992,067 B2 | 1/2006 | Glombik et al. |
| 7,067,689 B1 | 6/2006 | Renze et al. |
| 7,205,290 B2 | 4/2007 | Jaehne et al. |
| 7,388,004 B2 | 6/2008 | Jaehne et al. |
| 7,390,790 B2 | 6/2008 | Jaehne et al. |
| 7,407,938 B2 | 8/2008 | Jaehne et al. |
| 7,488,829 B2 | 2/2009 | Glombik et al. |
| 7,579,339 B2 | 8/2009 | Jaehne et al. |
| 7,671,047 B2 | 3/2010 | Jaehne et al. |
| 2003/0212070 A1 | 11/2003 | Schwink et al. |
| 2004/0077623 A1 | 4/2004 | Jaehne et al. |
| 2004/0082561 A1 | 4/2004 | Jaehne et al. |
| 2005/0239766 A1 | 10/2005 | Starke et al. |
| 2005/0267038 A1 | 12/2005 | Glombik et al. |
| 2007/0149501 A1 | 6/2007 | Jendralla et al. |
| 2007/0197498 A1 | 8/2007 | Jaehne et al. |
| 2008/0274947 A1 * | 11/2008 | Jaehne et al. ................. 540/200 |
| 2008/0281092 A1 | 11/2008 | Glombik et al. |
| 2008/0319218 A1 | 12/2008 | Haubrich et al. |
| 2008/0319221 A1 | 12/2008 | Junker et al. |
| 2010/0160282 A1 | 6/2010 | Glombik et al. |

FOREIGN PATENT DOCUMENTS

| | | |
|---|---|---|
| CA | 2 136 893 | 6/2002 |
| EP | 0 462 884 | 12/1991 |
| EP | 0 656 354 | 6/1995 |
| WO | WO 97/16455 A1 | 5/1997 |
| WO | WO 97/26265 A1 | 7/1997 |
| WO | WO 97/41097 A2 | 11/1997 |
| WO | WO 97/45406 A1 | 12/1997 |
| WO | WO 98/08871 A1 | 3/1998 |
| WO | WO 99/03861 A1 | 1/1999 |

(Continued)

OTHER PUBLICATIONS

Copending U.S. Appl. No. 11/155,109, filed Jun. 17, 2005, Glombik et al. Copending U.S. Appl. No. 11/767,284, filed Jun. 22, 2007, Haubrich et al.
Copending U.S. Appl. No. 12/219,196, filed Jul. 17, 2008, Glombik et al.
Copending U.S. Appl. No. 12/271,236, filed Nov. 13, 2008, Junker et al.
Castañer, R. M., et al., "Ezetimbe, Hypolipidemic Cholesterol Absorption Inhibitor SCH-58235," *Drugs of the Future* 2000, 25(7):679-685.

(Continued)

*Primary Examiner* — Mark Berch
(74) *Attorney, Agent, or Firm* — Finnegan, Henderson, Farabow, Garrett & Dunner, LLP

(57) ABSTRACT

Provided are certain crystalline hydrates of the formula I

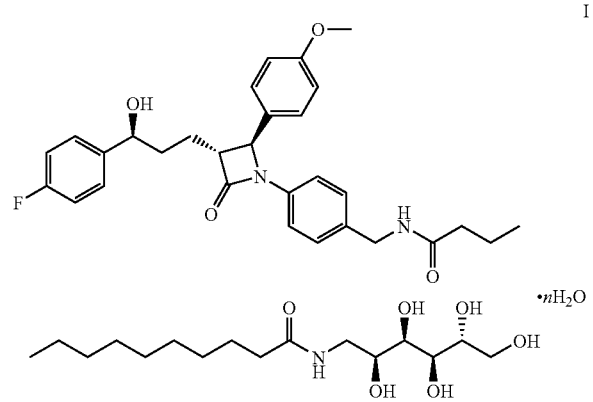

in which n has a value of from 0.5 to 1.8. The compound may be suitable, for example, as a hypolipidemic.

16 Claims, 3 Drawing Sheets

FOREIGN PATENT DOCUMENTS

| | | |
|---|---|---|
| WO | WO 99/15525 | 4/1999 |
| WO | WO 99/46262 | 9/1999 |
| WO | WO 00/34331 | 6/2000 |
| WO | WO 00/40569 | 7/2000 |
| WO | WO 00/63703 A1 | 10/2000 |
| WO | WO 00/64876 | 11/2000 |
| WO | WO 00/64888 | 11/2000 |
| WO | WO 00/71549 | 11/2000 |
| WO | WO 00/78312 | 12/2000 |
| WO | WO 01/04156 | 1/2001 |
| WO | WO 01/09111 | 2/2001 |
| WO | WO 01/62266 | 8/2001 |
| WO | WO 01/83451 | 11/2001 |
| WO | WO 01/85695 | 11/2001 |
| WO | WO 01/90094 | 11/2001 |
| WO | WO 02/44150 | 6/2002 |
| WO | WO 02/50027 | 6/2002 |
| WO | WO 03/015769 | 2/2003 |
| WO | WO 2009112203 A1 * | 9/2009 |

OTHER PUBLICATIONS

Goodman and Gilman's *The Pharmacological Basis of Therapeutics*, 10th Ed., 2001, p. 54.

Kosoglou, T., et al., "Coadministration of Simvastatin and Ezetimibe Leads to Significant Reduction in LDL-Cholesterol," *Proceedings of the 3rd International Congress on Coronary Artery Disease: From Prevention to Intervention*, 2000, p. 275.

Vaccaro, W. D., et al., "Sugar-Substituted 2-Azetidinone As Cholesterol Absorption Inhibitors," *Biorganic & Medicinal Chemistry Letters* 8(1998):35-40.

Vaccaro, W. D., et al., "Sugar-Substituted 2-Azetidinone Cholesterol Absorption Inhibitors: Enhanced Potency by Modification of the Sugar," *Biorganic & Medicinal Chemistry Letters* 8(1998):313-318.

van Heek, M., et al., "Comparison of the activity and disposition of the novel cholesterol absorption inhibitor, SCH58235, and its glucuronide, SCH60663," *British Journal of Pharmacology* 129:1748-1754 (2000).

Zaks, A., et al., "Enzymatic Glucuronidation of a Novel Cholesterol Absorption Inhibitor, SCH58235," *Applied Biochemistry and Biotechnology*, 73:205-214 (1998).

Non-Final Office Action for U.S. Appl. No. 10/021,502 (issued patent 6,992,067), mailed on Sep. 10, 2003, 4 pages.

Final Office Action for U.S. Appl. No. 10/021,502 (issued patent 6,992,067), mailed on Apr. 16, 2004, 11 pages.

Non-Final Office Action for U.S. Appl. No. 10/021,502 (issued patent 6,992,067), mailed on Aug. 25, 2004, 5 pages.

Non-Final Office Action for U.S. Appl. No. 10/021,502 (issued patent 6,992,067), mailed on Feb. 8, 2005, 9 pages.

Notice of Allowance for U.S. Appl. No. 10/021,502 (issued patent 6,992,067), mailed on Jul. 12, 2005, 4 pages.

Office Action for U.S. Appl. No. 10/813,954 (issued patent 7,205,290), mailed on May 18, 2006, 8 pages.

Notice of Allowance for U.S. Appl. No. 10/813,954 (issued patent 7,205,290), mailed on Nov. 27, 2006, 4 pages.

Office Action for U.S. Appl. No. 11/155,109 mailed on Aug. 17, 2006, 9 pages.

Final Office Action for U.S. Appl. No. 11/155,109 mailed on Feb. 14, 2007, 7 pages.

Office Action for U.S. Appl. No. 11/155,109 mailed on Jul. 16, 2007, 10 pages.

Final Office Action for U.S. Appl. No. 11/155,109 mailed on Jan. 9, 2008, 7 pages.

Notice of Panel Decision from Pre-Appeal Brief Review U.S. Appl. No. 11/155,109 mailed on May 2, 2008, 3 pages.

Examiner's Answer to Appeal Brief for U.S. Appl. No. 11/155,109 mailed on Aug. 6, 2008, 9 pages.

Office Action for U.S. Appl. No. 11/155,109 mailed on Dec. 3, 2008, 9 pages.

Notice of Allowance for U.S. Appl. No. 11/177,410 (issued patent 7,067,689), mailed on Mar. 31, 2006, 4 pages.

Office Action for U.S. Appl. No. 11/767,298, mailed Aug. 15, 2008, 5 pages.

Office Action for U.S. Appl. No. 11/797,720 (issued patent 7,488,829), mailed on Nov. 16, 2007, 6 pages.

Final Office Action for U.S. Appl. No. 11/797,720 (issued patent 7,488,829), mailed on Apr. 21, 2008, 8 pages.

Notice of Allowance for U.S. Appl. No. 11/797,720 (issued patent 7,488,829), mailed on Oct. 2, 2008, 6 pages.

Asakawa, A. et al., Cocaine-Amphetamine-Regulated Transcript Influences Energy Metabolism, Anxiety and Gastric Emptying in Mice, Hormone and Metabolic Research, 2001, vol. 33, No. 9, pp. 554-558.

Barf, T. et al., Arylsulfonamidothiazoles as a New Class of Potential Antidiabetic Drugs, Discovery of Potent and Selective Inhibitors of the 11 β-Hydroxysteroid Dehydrogenase Type 1, Journal of Medicinal Chemistry, 2002, vol. 45, No. 18, pp. 3813-3815.

Chaudhary, A. et al., $CO_2$ Offgas as a Mechanistic Probe and Scale-Up Tool in N-Acylations Using Mixed Anhydrides from Amino Acids and Isobutyl Chloroformate, Organic Process Research and Development, 2003, vol. 7, pp. 888-895.

Greene, T. et al., Protective Groups in Organic Synthesis, John Wiley and Sons, Inc., 1999, $3^{rd}$ Ed., pp. 1, 4-5, 372-374, 383-387, 415-419, 701-702, 705-707, and 728-731.

Ishihara, K. et al., 3,4,5-Trifluorobenzeneboronic Acid as an Extremely Active Amidation Catalyst, Journal of Organic Chemistry, 1996, vol. 61, pp. 4196-4197.

Klausner, Y. et al., Coupling Reagents' in Peptide Synthesis, Synthesis, 1972, No. 9, pp. 453-463.

Kunishima, M. et al., 4-(4,6-Dimethoxy-1,3,5-triazin-2-yl)-4-methyl-morpholinium Chloride: An Efficient Condensing Agent Leading to the Formation of Amides and Esters, Tetrahedron, 1999, vol. 55, pp. 13159-13170.

Larock, R., Interconversion of Nitriles, Carboxylic Acids and Derivatives, Comprehensive Organic Transformations: A Guide to Functional Group Preparations, VCH Publishers, New York, 1999, $2^{nd}$ Ed., pp. 1929-1930.

Lee, D. et al., Leptin Agonists as a Potential Approach to the Treatment of Obesity, Drugs of the Future, 2001, vol, 26, No. 9, pp. 873-881.

Okada, H. et al., Synthesis and Antitumor Activities of Prodrugs of Benzoylphenylureas, Chemical and Pharmaceutical Bulletin, 1994, vol. 42, No. 1, pp. 57-61.

Prata, C. et al., Charge-Reversal Amphiphiles for Gene Delivery, Journal of the American Chemical Society, 2004, vol. 126, pp. 12196-12197.

Prata, C. et al., Supporting Information for Charge Reversal Amphiphiles for Gene Delivery, Journal of the American Chemical Society, 2004, vol. 126, pp. S1-S8.

Saitoh, M. et al., Convenient Selective Monoesterification of α, ω-Dicarboxylic Acids Catalyzed by Ion-Exchange Resins, Tetrahedron Letters, 1996, vol. 37, No. 37, pp. 6733-6736.

Salvador, J. et al., Perspectives in the Therapeutic Use of Leptin, Expert Opinion Pharmacotherapy, 2001, vol. 2, No. 10, pp. 1615-1622.

Speicher, A. et al., O-(1-Benzotriazolyl)-$N,N,N',N'$-tetramethyluroniumhexafluorophosphat (HBTU) and O-(7-Aza-1-benzotriazolyl)-$N,N,N',N'$-tetrarnethyluroniunnhexafluorophosphat (HATU)-zwei moderne Kupplungsreagenzien zur Peptidsynthese, Journal für Praktische Chemie, 1998, vol. 340, pp. 581-583.

Zunft, H. et al., Carob Pulp Preparation for Treatment of Hypercholesterolemia, Advances in Therapy, 2001, vol. 18, No. 5, pp. 230-236.

* cited by examiner

CERTAIN CRYSTALLINE DIPHENYLAZETIDINONE HYDRATES, PHARMACEUTICAL COMPOSITIONS THEREOF AND METHODS FOR THEIR USE

This application claims the benefit of U.S. provisional application No. 60/990,255, filed Nov. 26, 2007, and German patent application no. 102007054497.0, filed Nov. 13, 2007. The contents of both priority documents are incorporated by reference herein.

Provided are certain crystalline hydrates of a substituted diphenylazetidinone.

Certain amorphous diphenylazetidinones are described in U.S. Pat. No. 7,205,290.

The crystalline polymorph or pseudopolymorph form of a particular drug may be a determinant, for example, of the drug's ease of preparation, stability, solubility, storage stability, ease of formulation and in vivo pharmacology. In cases where two or more polymorph substances can be produced, it may be desirable to have a method to make one or more of the polymorphs in pure form. In deciding which polymorph is to be used, the numerous properties of the polymorphs may be compared and a polymorph chosen based on the many physical property variables. It is entirely possible that one polymorph form can be more suitable in some circumstances where certain aspects such as ease of preparation, stability, etc., are deemed to be important. In other situations, a different polymorph may be more suitable for greater solubility and/or superior pharmacokinetics. Because improved drug formulations, showing, for example, better bioavailability or better stability are consistently sought, there is an ongoing need for new or purer polymorphic forms of existing drug molecules.

Provided is at least one crystalline hydrate of the formula I,

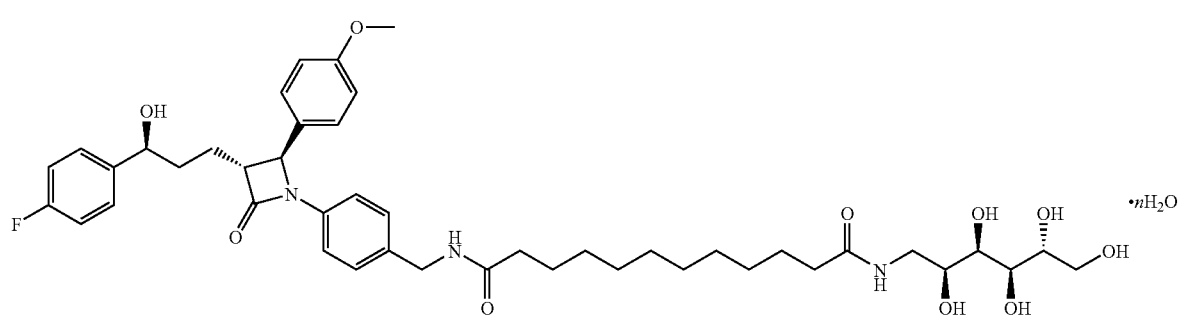

in which n has a value of from 0.5 to 1.8.

Also provided is a pharmaceutical composition comprising one or more pharmaceutically acceptable diluents and a therapeutically effective amount of at least one crystalline hydrate described herein. Also provided is a process for the preparation of a pharmaceutical composition described herein comprising formulating the therapeutically effective amount of at least one crystalline hydrate described herein with one or more pharmaceutically acceptable diluents to provide a composition suitable for administration. Also provided are uses of at least one crystalline hydrate described herein as a pharmaceutical.

Also provided is a method of treating a mammal having a lipid metabolism disorder comprising administering at least one crystalline hydrate described herein to the mammal. Also provided is a method of treating a mammal having a lipid metabolism disorder comprising formulating at least one crystalline hydrate described herein with one or more pharmaceutically acceptable diluents to form a composition and administering the composition to the mammal. Also provided is a use of at least one crystalline hydrate described herein for preparation of a medicament for the treatment of lipid metabolism disorders. Also provided is a process for the preparation of a medicament comprising at least one crystalline hydrate described herein for the treatment of lipid metabolism disorders.

Also provided is a method of treating a mammal having hyperlipidemia comprising administering at least one crystalline hydrate described herein to the mammal. Also provided is a method of treating a mammal having hyperlipidemia comprising formulating at least one crystalline hydrate described herein with one or more pharmaceutically acceptable diluents to form a composition and administering the composition to the mammal. Also provided is a use of at least one crystalline hydrate described herein for the preparation of a medicament for the treatment of hyperlipidemia. Also provided is a process for the preparation of a medicament comprising at least one crystalline hydrate described herein for the treatment of hyperlipidemia.

Also provided is a method of lowering the serum cholesterol level of a mammal comprising administering at least one crystalline hydrate described herein to the mammal. Also provided is a method of lowering the serum cholesterol level of a mammal comprising formulating at least one crystalline hydrate described herein with one or more pharmaceutically acceptable diluents to form a composition and administering the composition to the mammal. Also provided is a use of at least one crystalline hydrate described herein for the preparation of a medicament for lowering serum cholesterol level. Also provided is a process for the preparation of a medicament comprising at least one crystalline hydrate described herein for lowering serum cholesterol level.

Also provided is a process for the preparation of at least one crystalline hydrate described herein which comprises dissolving an amorphous compound of the formula II

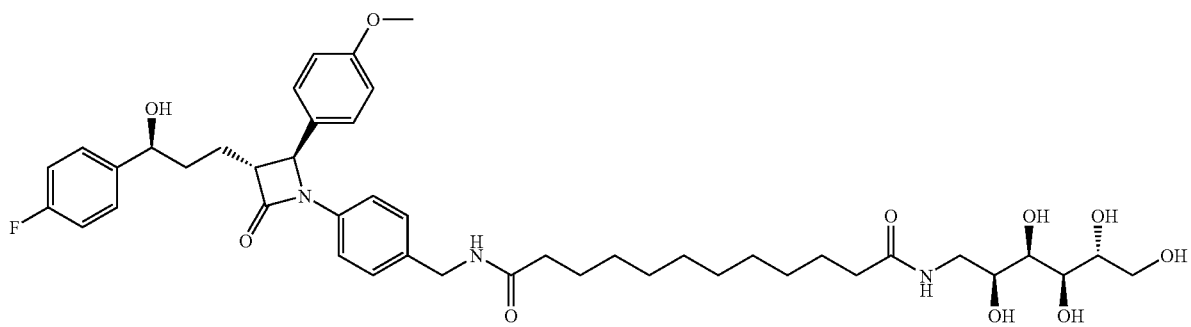

II in an organic solvent and adding the solution to a suspension of seed crystals of at least one crystalline hydrate of formula I. Also provided is a process for the preparation of at least one crystalline hydrate as described herein comprising purifying a compound of the formula II by chromatography and converting the purified compound of formula II to the at least one crystalline hydrate with water. Also provided is a process for the preparation of the at least one crystalline hydrate described herein comprising maintaining a compound of the formula II with a water content less than or equal to 1% under defined conditions of humidity, temperature, and time sufficient to produce at least one crystalline hydrate as described herein.

Figure 1:
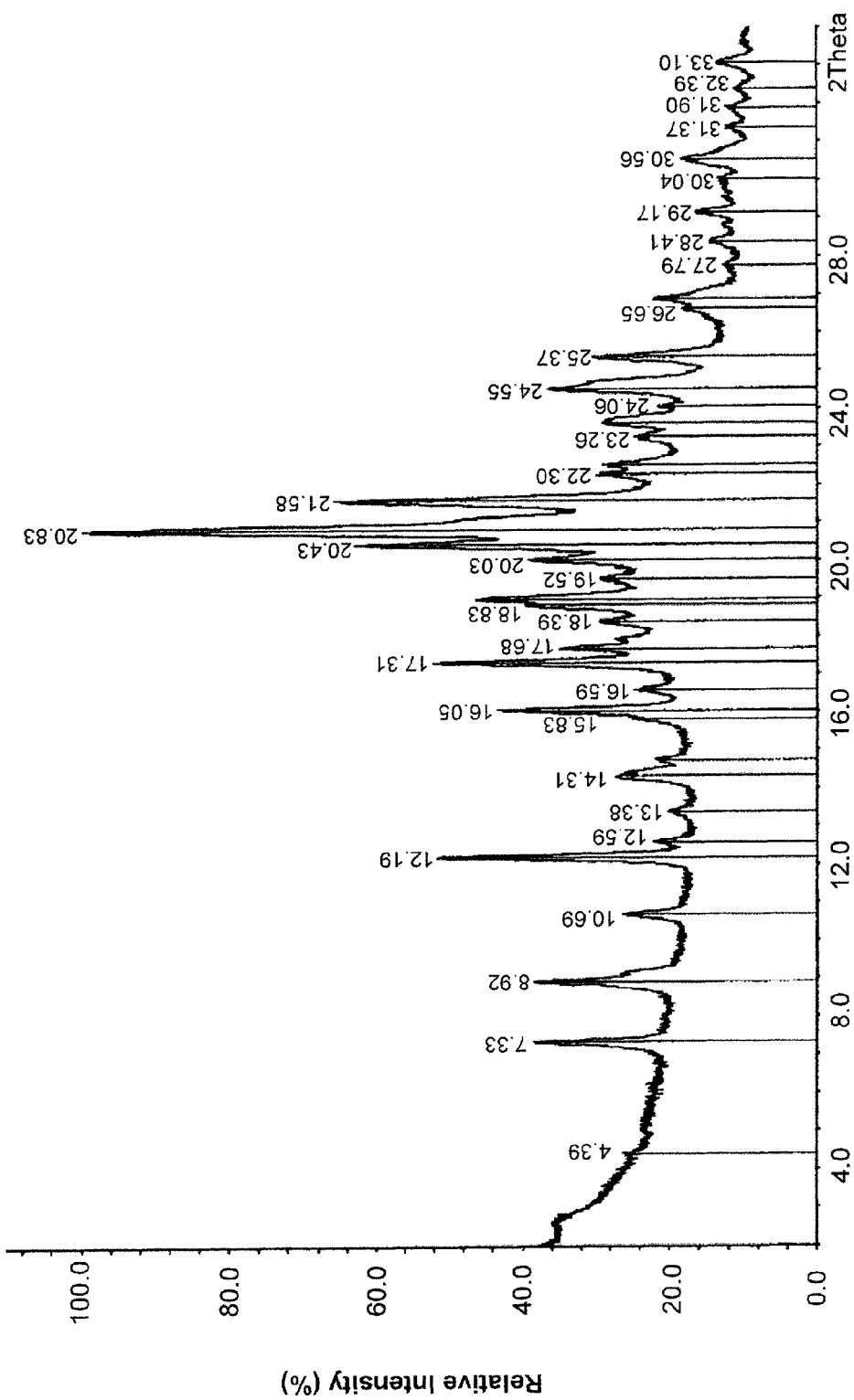
FIG. 1 shows the X-ray powder diffraction (XRPD) pattern of the crystalline hydrate of formula I prepared by Example 1.

The following abbreviations and terms have the indicated meanings throughout:

"Polymorphism" is defined as in the International Conference on Harmonization (ICH) Guideline Q6A Guideline: Specifications for New Drug Substances and Products: Chemical Substances, October 1999 and refers to the occurrence of different solid forms of the same drug substance. Polymorphs can be unsolvated or solvated crystal forms. Unsolvated crystal forms are crystals that do not have solvent incorporated within the crystal structure and include anhydrous crystal forms or anhydrates. Solvated crystal forms, or solvates, are crystalline solid adducts containing either stoichiometric or nonstoichiometric amounts of solvent molecules incorporated within the crystal structure. If the incorporated solvent is water, the solvates are also commonly known as hydrates. Amorphous solids consist of disordered arrangements of molecules and do not possess a distinguishable crystal lattice.

The term "solution" means a mixture of one or more solutes in one or more solvents. Solution is intended to encompass homogeneous mixtures as well as heterogeneous mixtures, such as slurries or other mixtures having a suspension of insoluble (not dissolved) material.

By a "detectable amount" is meant a sufficient amount to give positive identification but not necessarily quantitation of the compound by any suitable analytical technique, for example HPLC, XRPD, or other means.

The term "organic solvent" is broadly intended to mean any organic solvent. Examples include ethanol, acetone, methylene chloride, hexane, heptane, ethyl acetate, tetrahydrofuran, toluene, chloroform, and diethyl ether.

The term "therapeutically effective amount" of at least one crystalline hydrate of the formula I means an amount effective, when administered to a human or non-human patient, to provide be an amount sufficient to reduce lipid levels in the bloodstream or lower serum cholesterol.

Provided are crystalline hydrates of the formula I

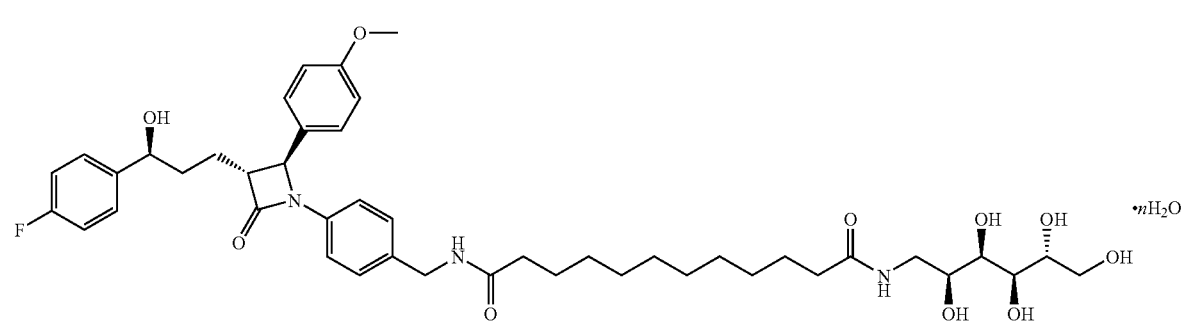

I in which n has a value of from 0.5 to 1.8 which correspond to a percentage by mass of water of about 1.1% to 4.0%.

In some embodiments, n has a value of from 0.8 to 1.3 which corresponds to a percentage by mass of water of about 1.8% to 2.9%. In some embodiments, n has a value of from 0.9 to 1.1 which corresponds to a percentage by mass of water of about 2.0% to 2.4%. In some embodiments, n has a value of 1 which corresponds to a percentage by mass of water of about 2.2%.

In some embodiments, the at least one crystalline hydrate of the formula I described herein contains no more than about 50% of any other polymorphic forms. In some embodiments, the at least one crystalline hydrate of the formula I described herein contain no more than about 10% of any other polymorphic forms. In some embodiments, the at least one crystalline hydrate of the formula I described herein contain no more than about 5% of any other polymorphic forms. In some embodiments, the at least one crystalline hydrate of the formula I described herein contain no more than about 1% of any other polymorphic forms.

In some embodiments, the at least one crystalline hydrate of the formula I described herein have a chemical purity of greater than about 95%. In some embodiments, the at least one crystalline hydrate of the formula I described herein have a chemical purity of greater than about 98%. In some embodiments, the at least one crystalline hydrate of the formula I described herein have a chemical purity of greater than about 99%. Chemical purity can be ascertained, for example, by high pressure liquid chromatography.

In some embodiments, the crystalline hydrates of the formula I described herein may be identified by one or more solid state analytical methods. For example, the crystalline hydrates of the formula I may be characterized according to one or more of, e.g., X-ray diffraction, unit cell constants, Fourier transform infrared spectroscopy, differential scanning calorimetry curve data, solid state nuclear magnetic resonance spectroscopy, and Raman spectroscopy. A sample is considered to be a crystalline hydrate of the formula I if it is characterized as a crystalline hydrate of the formula I by at least one of the above methods, regardless of any inconsistent or contradictory results obtained by any of the other methods described above. In addition, a sample is considered to be a crystalline hydrate of the formula I if it is characterized as a crystalline hydrate of the formula I by at least one of the above methods under a particular set of experimental conditions, regardless of any inconsistent or contradictory results obtained by the same method under a different set of experimental conditions.

In some embodiments, the crystalline hydrates of the formula I may be characterized according to melting point.

In some embodiments, the crystalline hydrates of the formula I may be characterized according to crystal habit.

For example, also provided is an embodiment of a crystalline hydrate of the formula I with an XRPD, measured with CuKα radiation, having a main peak of 20.83 degrees 2 theta±0.2 degrees 2 theta.

Also provided is an embodiment of a crystalline hydrate of the formula I with an XRPD, measured with CuKα radiation, having at least peaks of the following 2 theta values: 20.43, 20.83, and 21.58, each of the diffraction angles being ±0.2 degrees 2 theta.

Also provided is an embodiment of a crystalline hydrate of the formula I with an XRPD, measured with CuKα radiation, having at least peaks of the following 2 theta values: 12.19, 17.31, 20.43, 20.83, and 21.58, each of the diffraction angles being ±0.2 degrees 2 theta.

Also provided is an embodiment of a crystalline hydrate of the formula I with an XRPD, measured with CuKα radiation, having at least peaks of the following 2 theta values: 7.33, 8.92, 12.19, 16.05, 17.31, 17.68, 18.83, 20.43, 20.83, 21.58, 24.55, and 25.37, each of the diffraction angles being ±0.2 degrees 2 theta.

In some embodiments, the at least one crystalline hydrate of the formula I further comprises a detectable amount of at least one organic solvent. In some embodiments, the at least one organic solvent corresponds to at least one of the solvents initially incorporated within the crystal structure. In some embodiments, the at least one organic solvent corresponds to a solvent used during preparation, e.g., a solvent used in the crystallization, of the crystalline hydrate of the formula I. In some embodiments, the at least one crystalline hydrate of the formula I further comprises a detectable amount of ethanol.

In some embodiments, the at least one crystalline hydrate of the formula I may be useful for the treatment of lipid metabolism disorders. In some embodiments, the at least one crystalline hydrate of the formula I may be useful for the treatment of hyperlipidemia. In some embodiments, the at least one crystalline hydrate of the formula I may be useful for lowering serum cholesterol level.

The amount of the at least one crystalline hydrate of formula I necessary to achieve the desired biological effect depends on a number of factors, for example the specific compound chosen, the intended use, the mode of administration and the clinical condition of the patient. The daily dose is generally in the range from 0.01 mg to 100 mg (typically from 0.05 mg to 50 mg) per day and/or a range of the at least one crystalline hydrate of the formula I per kilogram of body weight, for example 0.05-10 mg/kg/day. Single-dose formulations which can be administered orally, such as, for example, tablets or capsules may contain, for example, from 1.0 to 1000 mg, typically from 5 to 600 mg.

For the therapy of the abovementioned conditions, the at least one crystalline hydrate of formula I may be used as the compound itself, but typically the at least one crystalline hydrate of formula I is in the form of a pharmaceutical composition with an acceptable carrier. The carrier is acceptable in the sense that it is compatible with the other ingredients of the composition and is not harmful for the patient's health. The carrier may be a solid or a liquid or both and may be formulated with at least one crystalline hydrate of formula I as a single dose, for example as a tablet, which may be prepared from 0.05% to 95% by weight of the at least one crystalline hydrate of formula I. Other active ingredients may likewise be present, including further crystalline hydrates of the formula I. The pharmaceutical compositions described herein can be produced by one of the known pharmaceutical methods, which essentially consist of mixing the ingredients with pharmacologically acceptable carriers and/or excipients.

In some embodiments, the composition may contain only a single form of the crystalline hydrate of the formula I, such as where n is 1, or a mixture of various forms of the crystalline hydrate, with or without amorphous form. In some embodiments, the at least one crystalline hydrate of the formula I is converted, in whole or in part, to one or more other forms, including a non-solid form, upon formulation with the one or more pharmaceutically acceptable diluents. In some embodiments, the at least one crystalline hydrate of formula I is dissolved when formulated. Accordingly, in such cases, the compound of formula I no longer exists in crystalline form in the composition.

Pharmaceutical compositions described herein are those suitable for oral and peroral (for example sublingual) administration, although the suitable mode of administration may depend in each individual case on the nature and severity of the condition to be treated and on the nature of the at least one crystalline hydrate of formula I used in each case to prepare the pharmaceutical composition. Coated formulations and coated slow-release formulations also are provided. Acid- and gastric juice-resistant formulations are possible. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compositions for oral administration prepared from at least one crystalline hydrate of formula I may be in the form of separate units such as, for example, capsules, cachets, suckable tablets or tablets, each of which is prepared with a defined amount of at least one crystalline hydrate of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which at least one crystalline hydrate of formula I and a carrier (which may consist of one or more additional ingredients) are brought into contact. The compositions are generally produced by uniform and homogeneous mixing of at least one crystalline hydrate of formula I with a liquid and/or finely divided solid carrier, after which the product is shaped if necessary. Thus, for example, a tablet can be produced by compressing or molding a powder or granules of at least one crystalline hydrate of formula I, where appropriate with one or more additional ingredients. Compressed tablets can be produced by tableting at least one crystalline hydrate of formula I in free-flowing form such as, for example, a powder or granules, where appropriate mixed with a binder, glidant, inert diluent and/or one (or more) surface-active/dispersing agent(s) in a suitable machine. Molded tablets can be produced by molding at least one crystalline hydrate of formula I, which is in powder form and is moistened with an inert liquid diluent, in a suitable machine. Compositions can also be prepared by wet granulation. Thus, for example, a composition can be prepared by wet granulation by mixing the at least one crystalline hydrate of formula I, one or more optional additional ingredients, a suitable solvent, and a binder to prepare a wet granulate, drying the wet granulate, and milling the dried granulate. The method may further comprise adding at least one lubricant to the dried milled granulate and compressing the dried milled granulate to form tablets. The optional additional ingredients may include, for example, at least one diluent and/or at least one disintegration agent. The suitable solvent can be water. In some embodiments, the diluent comprises calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, or starch. In some embodiments, the diluent is present in an amount of about 35% to about 90% by weight of the tablet. In some embodiments, the binder comprises acacia, alginic acid, carbomer, sodium carboxymethylcellulose, dextrin, ethylcellulose, gelatin, glucose, guar gum, hydroxypropyl cellulose, maltose, methylcellulose, polyethylene oxide, or povidone. In some embodiments, the binder is present in an amount of about 0.5% to about 5% by weight of the tablet.

Pharmaceutical compositions which are suitable for peroral (sublingual) administration comprise suckable tablets which are prepared from at least one crystalline hydrate of formula I with a flavoring, normally sucrose and gum arabic or tragacanth, and pastilles The at least one crystalline hydrate of formula I described herein can also be administered in combination with further active ingredients. When administered as a combination, the active ingredients can be formulated as separate compositions that are administered at the same time or sequentially at different times, or the active ingredients can be administered in a single composition, provided that the active ingredients are not incompatible with other active ingredients or the formulation, or otherwise undesirably combined in a single composition.

The phrase "co-therapy" (or "combination-therapy") or "in combination with", as used herein, defines the use of at least one crystalline hydrate of formula I as described herein and one or more further active ingredients, such as, for example:

administration of each active ingredient in a sequential manner in a regimen to provide beneficial effects of the drug combination; and/or co-administration of the aforementioned components in a substantially simultaneous manner (e.g., as in a single capsule having a fixed ratio of the active ingredients or in multiple, separate capsules for each active ingredient, etc.).

Thus, methods described herein are not limited in the sequence of administration; the at least one crystalline hydrate of formula I may be administered either prior to, at the same time with or after administration of the further active ingredient(s).

Further exemplary active ingredients suitable for combination products include: all antidiabetics which are mentioned in the Rote Liste 2007, chapter 12; all weight-reducing agents/appetite suppressants which are mentioned in the Rote Liste 2005, chapter 1; and all lipid-lowering agents which are mentioned in the Rote Liste 2007, chapter 58, the disclosures of which are incorporated by reference herein. They may be administered with at least one crystalline hydrate of formula I described herein in particular for a synergistic improvement in the effect. Synergy can be in terms of lower incidence or severity of side effects, increased therapeutic effect, or some other beneficial effect of the combination compared with the individual components. In some embodiments, when the at least one crystalline hydrate of formula I is administered with a statin drug, such as atorvastatin, a lower amount of the statin can be used and achieve the same lipid lowering that would be achieved with a higher amount of the statin and/or achieve reduced side effects. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or Levemir® (insulin detemir) or those described in WO2005005477 (Novo Nordisk), fast-acting insulins such as Apidra® (see U.S. Pat. No. 6,221,633), inhalable insulins such as, for example, Exubera® or oral insulins such as, for example, IN-1 05 (Nobex) or Oral-lyn™ (Generex Biotechnology), GLP-1 derivatives and GLP-1 agonists such as, for example, exenatide, liraglutide or those which have been disclosed in WO98/08871 or WO2005027978, WO2006037811, WO2006037810 of Novo Nordisk NS, in WO01/04156 of Zealand or in WO00/34331 of Beaufour-Ipsen, pramlintide acetate (Symlin; Amylin Pharmaceuticals), BIM-51077, PC-DAC:exendin-4 (an exendin-4 analog covalently bonded to recombinant human albumin), agonists like those described for example in D. Chen et al., Proc. Natl. Acad. Sci. USA 104 (2007) 943, those described in WO2006124529, and orally effective hypoglycemic active ingredients.

Antidiabetics also include agonists of the glucose-dependent insulinotropic polypeptide (GIP) receptor as described for example in WO2006121860.

The orally effective hypoglycemic active ingredients include, for example, sulfonylureas, biguanidines, meglitinides, oxadiazolidinediones, thiazolidinediones, glucosidase inhibitors, inhibitors of glycogen phosphorylase, glucagon antagonists, glucokinase activators, inhibitors of fructose-1,6-bisphosphatase, modulators of glucose transporter 4 (GLUT4), inhibitors of glutamine-fructose-6-phosphate amidotransferase (GFAT), GLP-1 agonists, potassium channel openers such as, for example, pinacidil, cromakalim, diazoxide or those described in R. D. Carr et al., Diabetes 52, 2003, 2513-2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97126265 and WO 99/03861 of Novo Nordisk AIS, inhibitors of dipeptidylpeptidase IV (DPP-IV), insulin sensitizers, inhibitors of liver enzymes involved in stimulating gluconeogenesis and/or glycogenolysis, modulators of glucose uptake, of glucose transport and of glucose reabsorption, inhibitors of 11βHSD1, inhibitors of protein tyrosine phosphatase 1 B (PTPI B), modulators of the sodium-dependent glucose transporter 1 or 2 (SGLT1, SGLT2), compounds which alter lipid metabolism such as antihyperlipidemic active ingredients and antilipidemic active ingredients, compounds which reduce feed intake, compounds which increase thermogenesis, PPAR and RXR modulators and active ingredients which act on the ATP-dependent potassium channel of the beta cells.

In some embodiments, the at least one crystalline hydrate of formula I is administered in combination with a HMGCoA reductase inhibitor, commonly known as a statin, such as simvastatin, fluvastatin, pravastatin, lovastatin, atorvastatin, cerivastatin, rosuvastatin, or L-659699. In some embodiments, the at least one crystalline hydrate of formula I is administered in combination with atorvastatin. In some embodiments, the pharmaceutical composition comprises 1-50 mg of atorvastatin and 10-50 mg of at least one crystalline hydrate of formula I. In some embodiments, the pharmaceutical composition comprises 5-15 mg of atorvastatin and 15-50 mg of at least one crystalline hydrate of formula I. In some embodiments, the pharmaceutical composition comprises 10 mg of atorvastatin and 25 mg of at least one crystalline hydrate of formula I. In some embodiments, the pharmaceutical composition comprises 10 mg of atorvastatin and 50 mg of at least one crystalline hydrate of formula I.

In some embodiments, the at least one crystalline hydrate of formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.), or WO2005044256 or WO2005062824 (Merck & Co.) or WO2005061451 and WO2005061452 (AstraZeneca AB), and WO2006017257 (Phenomix) or WO2005033100 (Lipideon Biotechnology AG) or as described in WO2004097655, WO2004000805, WO2004000804, WO2004000803, WO2002050068, WO2002050060, WO2005047248, WO2006086562, WO2006102674, WO2006116499, WO2006121861, WO2006122186, WO200622216, WO2006127893, WO2006137794, WO2006137796, WO2006137782, WO2006137793, WO2006137797, WO2006137795, WO2006137792, and WO2006138163.

In some embodiments, the at least one crystalline hydrate of formula I is administered in combination with Vytorin™, a fixed combination of ezetimibe with simvastatin.

In some embodiments, the at least one crystalline hydrate of formula I is administered in combination with a fixed combination of ezetimibe with atorvastatin.

In some embodiments, the at least one crystalline hydrate of formula I is administered in combination with a fixed combination of ezetimibe with fenofibrate.

In some embodiments, the at least one crystalline hydrate of formula I is administered in combination with a fixed combination of fenofibrate with rosuvastatin.

In some embodiments, the at least one crystalline hydrate of formula I is administered in combination with synordia (R), a fixed combination of fenofibrate with metformin.

In some embodiments, the at least one crystalline hydrate of formula I is administered in combination with ISIS-301012, an antisense oligonucleotide able to regulate the apolipoprotein B gene.

In some embodiments, the at least one crystalline hydrate of formula I is administered in combination with a PPAR gamma agonist such as, for example, rosiglitazone, pioglitazone, JTT-501, GI 262570, R-483 or CS-01 (rivoglitazone).

In some embodiments, the at least one crystalline hydrate of formula I is administered in combination with Competact™, a fixed combination of pioglitazone hydrochloride with metformin hydrochloride.

In some embodiments, the at least one crystalline hydrate of formula I is administered in combination with Tandemact™, a fixed combination of pioglitazone with glimepride.

In some embodiments, the at least one crystalline hydrate of formula I is administered in combination with a fixed combination of pioglitazone hydrochloride with an angiotensin II agonist such as, for example, TAK-536.

In some embodiments, the at least one crystalline hydrate of formula I is administered in combination with a PPAR alpha agonist such as, for example, GW9578, GW-590735, K-111, LY-674, KRP-101, DRF-10945, or LY-518674 or those described in WO2001040207, WO2002096894, and WO2005097076.

In some embodiments, the at least one crystalline hydrate of formula I is administered in combination with a mixed PPAR alpha/gamma agonist such as, for example, naveglitazar, LY-510929, ONO-5129, E-3030, AVE 8042, AVE 8134, AVE 0847, or CKD-501 (lobeglitazone sulfate) or as described in WO 00/64888, WO 00/64876, WO 03/020269 or in J. P. Berger et al., TRENDS in Pharmacological Sciences 28(5), 244-251, 2005.

In some embodiments, the at least one crystalline hydrate of formula I is administered in combination with a PPAR delta agonist such as, for example, GW-501516 or as described in WO2006059744, WO2006084176, WO2006029699, WO2007039172, and WO2007039178.

In some embodiments, the at least one crystalline hydrate of formula I is administered in combination with metaglidasen or with MBX-2044 or other partial PPAR gamma agonists/antagonists.

In some embodiments, the at least one crystalline hydrate of formula I is administered in combination with a fibrate such as, for example, fenofibrate, clofibrate or bezafibrate.

In some embodiments, the at least one crystalline hydrate of formula I is administered in combination with an MTP inhibitor such as, for example, implitapide, BMS-201038, R-103757, AS-1552133 or those described in WO2005085226, WO2005121091, and WO2006010423.

In some embodiments, the at least one crystalline hydrate of formula I is administered in combination with a CETP inhibitor such as, for example, torcetrapib or JTT-705 or those described in WO2006002342, WO2006010422, WO2006012093, WO2006073973, WO2006072362, WO2006097169, and WO2007041494.

In some embodiments, the at least one crystalline hydrate of formula I is administered in combination with a bile acid absorption inhibitor (see, for example, U.S. Pat. No. 6,245,744, U.S. Pat. No. 6,221,897 or WO00/61568), such as, for example, HMR 1741 or those as described in DE 10 2005 033099.1 and DE 10 2005 033100.9 and WO2007009655-56.

In some embodiments, the at least one crystalline hydrate of formula I is administered in combination with a polymeric bile acid adsorbent such as, for example, cholestyramine or colesevelam.

In some embodiments, the at least one crystalline hydrate of formula I is administered in combination with an LDL receptor inducer (see U.S. Pat. No. 6,342,512), such as, for example, HMR1171, HMR1586 or those as described in WO2005097738.

In some embodiments, the at least one crystalline hydrate of formula I is administered in combination with an ABCA1 expression enhancer as described for example in WO2006072393.

In some embodiments, the at least one crystalline hydrate of formula I is administered in combination with an RNAi therapeutic directed against PCSK9 (proprotein convertase subtilisin/kexin type 9).

In some embodiments, the at least one crystalline hydrate of formula I is administered in combination with Omacor® (omega-3 fatty acids; highly concentrated ethyl esters of eicosapentaenoic acid and of docosahexaenoic acid).

In some embodiments, the at least one crystalline hydrate of formula I is administered in combination with an ACAT inhibitor such as, for example, avasimibe or SMP-797.

In some embodiments, the at least one crystalline hydrate of formula I is administered in combination with an antioxidant such as, for example, OPC-14117, probucol, tocopherol, ascorbic acid, β-carotene or selenium.

In some embodiments, the at least one crystalline hydrate of formula I is administered in combination with a vitamin such as, for example, vitamin B6 or vitamin B12.

In some embodiments, the at least one crystalline hydrate of formula I is administered in combination with a lipoprotein lipase modulator such as, for example, ibrolipim (NO-1886).

In some embodiments, the at least one crystalline hydrate of formula I is administered in combination with an ATP citrate lyase inhibitor such as, for example, SB-204990.

In some embodiments, the at least one crystalline hydrate of formula I is administered in combination with a squalene synthetase inhibitor such as, for example, BMS-188494, TAK-475 or as described in WO2005077907 and JP2007022943.

In some embodiments, the at least one crystalline hydrate of formula I is administered in combination with a lipoprotein (a) antagonist such as, for example, gemcabene (CI-1027).

In some embodiments, the at least one crystalline hydrate of formula I is administered in combination with an agonist of GPRl O9A (HM74A receptor agonist; NAR (nicotinic acid receptor) agonist such as, for example, nicotinic acid or extended release niacin in conjunction with MK-0524A or the compounds described in WO2006045565, WO2006045564, WO2006069242, WO2006124490, WO2006113150, WO2007017261, WO2007017262, WO2007017265, WO20070115744, and WO2007027532.

In some embodiments, the at least one crystalline hydrate of formula I is administered in combination with an agonist of GPR116 as described for example in WO2006067531 and WO2006067532.

In some embodiments, the at least one crystalline hydrate of formula I is administered in combination with a lipase inhibitor such as, for example, orlistat or cetilistat (ATL-962).

In some embodiments, the at least one crystalline hydrate of formula I is administered in combination with insulin.

In some embodiments, the at least one crystalline hydrate of formula I is administered in combination with a sulfonylurea such as, for example, tolbutamide, glibenclamide, glipizide or glimepiride.

In some embodiments, the at least one crystalline hydrate of formula I is administered in combination with a substance which enhances insulin secretion, such as, for example, KCP-265 (WO2003097064) or those described in WO2007026761.

In some embodiments, the at least one crystalline hydrate of formula I is administered in combination with agonists of the glucose-dependent insulinotropic receptor (GDIR), such as, for example, APD-668.

In some embodiments, the at least one crystalline hydrate of formula I is administered in combination with a biguanide such as, for example, metformin.

In some embodiments, the at least one crystalline hydrate of formula I is administered in combination with a meglitinide such as, for example, repaglinide, nateglinide or mitiglinide.

In some embodiments, the at least one crystalline hydrate of formula I is administered with a combination of mitiglinide with a glitazone, e.g. pioglitazone hydrochloride.

In some embodiments, the at least one crystalline hydrate of formula I is administered with a combination of mitiglinide with an alpha-glucosidase inhibitor.

In some embodiments, the at least one crystalline hydrate of formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In some embodiments, the at least one crystalline hydrate of formula I is administered in combination with an α-glucosidase inhibitor such as, for example, miglitol or acarbose.

In some embodiments, the at least one crystalline hydrate of formula I is administered in combination with an active ingredient which acts on the ATP-dependent potassium channel of the beta cells, such as, for example, tolbutamide, glibenclamide, glipizide, glimepiride or repaglinide.

In some embodiments, the at least one crystalline hydrate of formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In some embodiments, the at least one crystalline hydrate of formula I is administered in combination with an inhibitor of glycogen phosphorylase, such as, for example, PSN-357 or FR-258900 or those as described in WO2003084922, WO2004007455, WO2005073229-31 or WO2005067932.

In some embodiments, the at least one crystalline hydrate of formula I is administered in combination with glucagon receptor antagonists such as, for example, A-770077, NNC-25-2504 or as described in WO2004100875 or WO2005065680.

In some embodiments, the at least one crystalline hydrate of formula I is administered in combination with activators of glucokinase, such as, for example, LY-2121260 (WO2004063179), PSN-105, PSN-110, GKA-50 or those as are described for example in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, and WO20070518467.

In some embodiments, the at least one crystalline hydrate of formula I is administered in combination with an inhibitor of gluconeogenesis, such as, for example, FR-225654.

In some embodiments, the at least one crystalline hydrate of formula I is administered in combination with inhibitors of fructose-1,6-bisphosphatase (FBPase), such as, for example, CS-917 (MB-06322) or MB-07803 or those described in WO2006023515, WO2006104030, and WO2007014619.

In some embodiments, the at least one crystalline hydrate of formula I is administered in combination with modulators of glucose transporter 4 (GLUT4), such as, for example, KST-48 (D.-O. Lee et al.: Arzneim.-Forsch. Drug Res. 54 (12), 835 (2004)).

In some embodiments, the at least one crystalline hydrate of formula I is administered in combination with inhibitors of glutamine-fructose-6-phosphate amidotransferase (GFAT), as are described for example in WO2004101528.

In some embodiments, the at least one crystalline hydrate of formula I is administered in combination with inhibitors of dipeptidylpeptidase IV (DPP-IV), such as, for example, vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200, GW-825964X, KRP-104, DP-893, ABT-341, ABT-279 or another salt thereof, or the compounds described in WO2003074500, WO2003106456, WO2004037169, WO200450658, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006090915, WO2006104356, WO2006127530, WO2006111261, WO2007015767, WO2007024993, and WO2007029086.

In some embodiments, the at least one crystalline hydrate of formula I is administered in combination with Janumet™, a fixed combination of sitagliptin phosphate with metformin hydrochloride.

In some embodiments, the at least one crystalline hydrate of formula I is administered in combination with inhibitors of 11-beta-hydroxysteroid dehydrogenase 1 (11β-HSD1), such as, for example, BVT-2733, JNJ-25918646, INCB-13739 or those as are described for example in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, and WO2007051810.

In some embodiments, the at least one crystalline hydrate of formula I is administered in combination with inhibitors of protein tyrosine phosphatase 1B (PTP1B), as are described for example in WO200119830-31, WO200117516, WO2004506446, WO2005012295, WO2005116003, WO2005116003, WO2006007959, DE 10 2004 060542.4, WO2007009911, WO2007028145, and WO2007081755.

In some embodiments, the at least one crystalline hydrate of formula I is administered in combination with modulators of the sodium-dependent glucose transporter 1 or 2 (SGLT1, SGLT2), such as, for example, KGA-2727, T-1095, SGL-0010, AVE 2268, SAR 7226 and sergliflozin or as are described for example in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, and WO2007080170 or by A. L. Handlon in Expert Opin. Ther. Patents (2005) 15(11), 1531-1540.

In some embodiments, the at least one crystalline hydrate of formula I is administered in combination with modulators of GPR40 as described for example in WO2007013689 and WO2007033002.

In some embodiments, the at least one crystalline hydrate of formula I is administered in combination with modulators of GPR119b as described for example in WO2004041274.

In some embodiments, the at least one crystalline hydrate of formula I is administered in combination with modulators of GPR119 as described for example in WO2005061489 (PSN-632408), WO2004065380, WO2007003960-62 and WO2007003964.

In some embodiments, the at least one crystalline hydrate of formula I is administered in combination with modulators of GPR120.

In some embodiments, the at least one crystalline hydrate of formula I is administered in combination with inhibitors of hormone-sensitive lipase (HSL) and/or phospholipases as described for example in WO2005073199, WO2006074957, WO2006087309, WO2006111321, and WO2007042178.

In some embodiments, the at least one crystalline hydrate of formula I is administered in combination with inhibitors of acetyl-CoA carboxylase (ACC), such as, for example, those as described in WO199946262, WO200372197, WO2003072197, WO02005044814, WO2005108370, JP2006131559, WO2007011809, WO2007011811, and WO2007013691.

In some embodiments, the at least one crystalline hydrate of formula I is administered in combination with modulators of xanthine oxidoreductase (XOR).

In some embodiments, the at least one crystalline hydrate of formula I is administered in combination with an inhibitor of phosphoenolpyruvate carboxykinase (PEPCK), such as, for example, those as described in WO2004074288.

In some embodiments, the at least one crystalline hydrate of formula I is administered in combination with an inhibitor of glycogen synthase kinase 3 beta (GSK-3 beta), as described for example in US2005222220, WO2005085230, WO2005111018, WO2003078403, WO2004022544, WO20031064101, WO2005058908, US2005038023, WO2005009997, US2005026984, WO2005000836, WO2004106343, EP1460075, WO2004014910, WO2003076442, WO2005087727 and WO2004046117.

In some embodiments, the at least one crystalline hydrate of formula I is administered in combination with an inhibitor of the serum/glucocorticoid-regulated kinase (SGK) as described for example in WO2006072354.

In some embodiments, the at least one crystalline hydrate of formula I is administered in combination with an agonist of the RUP3 receptor as described for example in WO2007035355.

In some embodiments, the at least one crystalline hydrate of formula I is administered in combination with an inhibitor of protein kinase C beta (PKC beta), such as, for example, ruboxistaurin.

In some embodiments, the at least one crystalline hydrate of formula I is administered in combination with an activator of the gene which codes for the ataxia telangiectasia mutated (ATM) protein kinase, such as, for example, chloroquine.

In some embodiments, the at least one crystalline hydrate of formula I is administered in combination with an endothelin A receptor antagonist such as, for example, avosentan (SPP-301).

In some embodiments, the at least one crystalline hydrate of formula I is administered in combination with inhibitors of "I-kappaB kinase" (IKK inhibitors), as are described for example in WO2001000610, WO2001030774, WO2004022553 and WO2005097129.

In some embodiments, the at least one crystalline hydrate of formula I is administered in combination with modulators of the glucocorticoid receptor (GR), like those described for example in WO2005090336, WO2006071609, and WO2006135826.

In some embodiments, the at least one crystalline hydrate of formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558); NPY antagonists such as, for example, naphthalene-1-sulfonic acid {4-[(4-amino-quinazolin-2-ylamino)methyl]cyclohexylmethyl}amide hydrochloride (CGP 71683A); NPY-5 receptor antagonists such as L-152804 or such as described, for example, in WO2006001318; NPY-4 receptor antagonists such as described, for example, in WO2007038942; NPY-2 receptor antagonists such as described, for example, in WO2007038943; peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424 and WO2006095166; derivatives of the peptide obestatin such as those described in WO2006096847; CB1R (cannabinoid receptor 1) antagonists (such as, for example, rimonabant, SR147778, SLV-319, AVE-1625, MK-0364 or salts thereof or compounds such as those described for example in EP 0656354, WO 00/115609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737, WO2007084319, and WO2007084450); cannabinoid receptor 1/cannabinoid receptor 2 (CB1/CB2) modulating compounds as described for example in WO2007001939, WO2007044215, WO2007047737; MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; WO 01/91752) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, US20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052; orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458, and WO2006067224); histamine H3 receptor agonists (e.g. 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893, WO2006107661, WO2007003804, WO2007016496, and WO2007020213); histamine H1/histamine H3 modulators such as, for example, betahistine or its dihydrochloride; CRF antagonists (e.g. [2-methyl-9-(2,4,6-trimethylphenyl)-9H-1,3,9-triazafluoren-4-yl]dipropylamine (WO 00/166585)); CRF BP antagonists (e.g. urocortin); urocortin agonists; agonists of the beta-3 adrenoceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as are described in JP2006111553, WO2002038543, and WO2007048840-843; MSH (melanocyte-stimulating hormone) agonists; MCH (melanin-concentrating hormone) receptor antagonists (such as, for example, NBI-845, A-761, A-665798, A-798, ATC-0175, T-226296, T-71, GW-803430 or compounds such as are described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, and JP2007091649); CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) and SR-146131 (WO 0244150) and SSR-125180) or those as are described in WO2005116034; serotonin reuptake inhibitors (e.g. dexfenfluramine); mixed serotonin/dopamine reuptake inhibitors (e.g. bupropion) or fixed combinations of bupropion with naltrexone; mixed serotoninergic and noradrenergic compounds (e.g. WO 00/71549); 5-HT receptor agonists, e.g. 1-(3-ethylbenzofuran-7-yl)piperazine oxalic acid salt (WO 01/09111); mixed dopamine/norepinephrine/acetylcholine reuptake inhibitors (e.g. tesofensine); 5-HT2C receptor agonists (such as, for example, lorcaserin hydrochloride (APD-356) or BVT-933 or those as are described in WO200077010, WO200077001-02, WO2005019180, WO2003064423, WO200242304, WO2005035533, WO2005082859, WO2006077025, and WO2006103511); 5-HT6 receptor modulators such as, for example E-6837 or BVT-74316 or those as are described in WO2005058858 and WO2007054257; bombesin receptor agonists (BRS-3 agonists); galanin receptor antagonists; growth hormone (e.g. human growth hormone or AOD-9604); growth hormone-releasing compounds (tertiary butyl 6-benzyloxy-1-(2-diisopropylaminoethylcarbamoyl)-3,4-dihydro-1H-isoquinoline-2-carboxylate (WO 01/85695)); growth hormone secretagogue receptor antagonists (ghrelin antagonists) such as, for example, A-778193 or those as are described in WO2005030734; TRH agonists (see, for example, EP 0 462 884); uncoupling protein 2 or 3 modulators; leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881); DA agonists (bromocriptine or Doprexin); lipase/amylase inhibitors (for example WO 00/40569); inhibitors of diacylglycerol O-acyltransferases (DGATs) such as for example BAY-74-4113 or as described for example in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538; inhibitors of fatty acid synthase (FAS) such as, for example, C75 or those as described in WO2004005277; inhibitors of stearoyl-CoA delta9 desaturase (SCD1) as described for example in WO2007009236, WO2007044085, WO2007046867, WO2007046868, WO20070501124; oxyntomodulin; oleoylestrone or thyroid hormone receptor agonists or partial agonists such as, for example: KB-2115 or those as described in WO2005058279, WO200172692, WO200194293, WO2003084915, WO2004018421, WO2005092316, WO2007003419, WO2007009913, and WO2007039125.

In some embodiments, the further active ingredient is varenicline tartrate, a partial agonist of the alpha 4-beta 2 nicotinic acetylcholine receptor.

In some embodiments, the further active ingredient is trodusquemine.

In some embodiments, the further active ingredient is a modulator of the SIRT1 enzyme.

In some embodiments, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In some embodiments, the further active ingredient is dexamphetamine or amphetamine.

In some embodiments, the further active ingredient is fenfluramine or dexfenfluramine.

In some embodiments, the further active ingredient is sibutramine.

In some embodiments, the further active ingredient is mazindole or phentermine.

In some embodiments, the at least one crystalline hydrate of formula I is administered in combination with bulking agents, such as insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can in this connection also be administered in the form of food products such as, for example, in bakery products or muesli bars.

It will be understood that every suitable combination of the compounds of the invention with one or more of the aforementioned compounds and optionally one or more further active ingredients will be regarded as falling within the protection conferred by the present invention.

Exemplary compounds are set forth below.

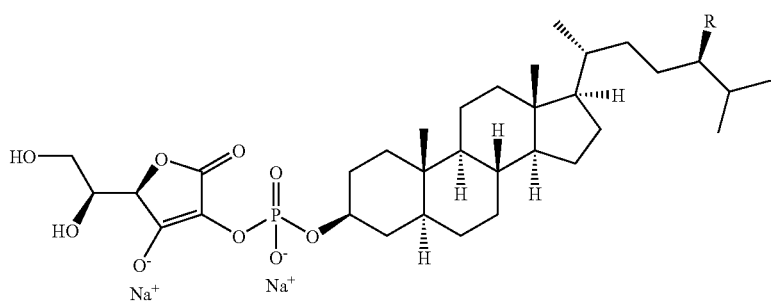

FM-VP4

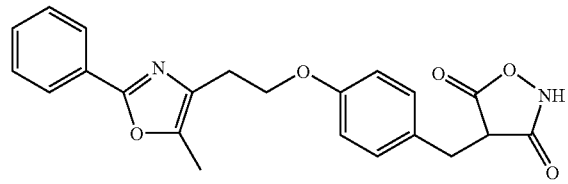
JTT-501
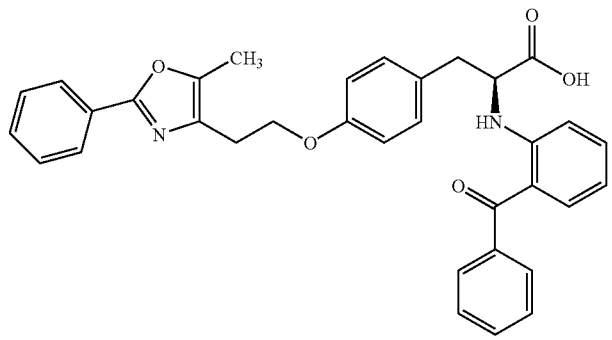
GI 262570
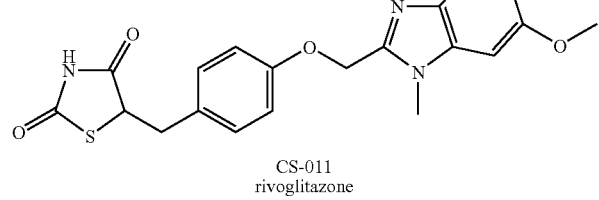
CS-011
rivoglitazone
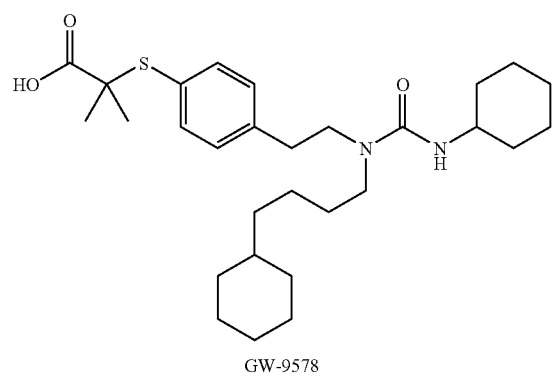
GW-9578
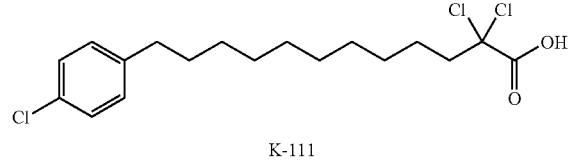
K-111
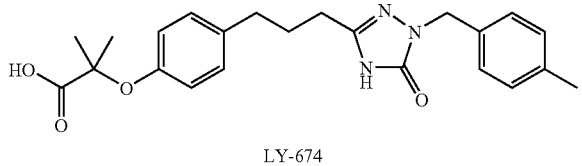
LY-674
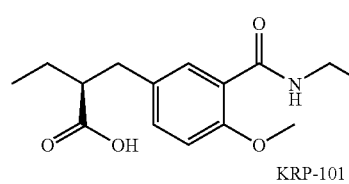
KRP-101
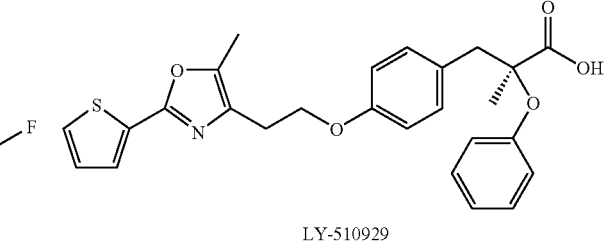
LY-510929
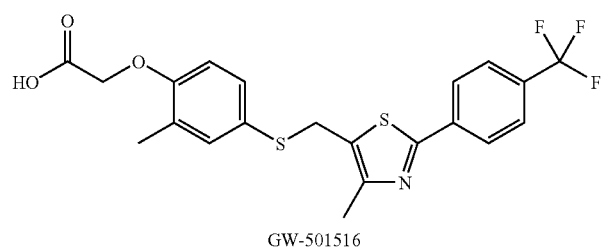
GW-501516
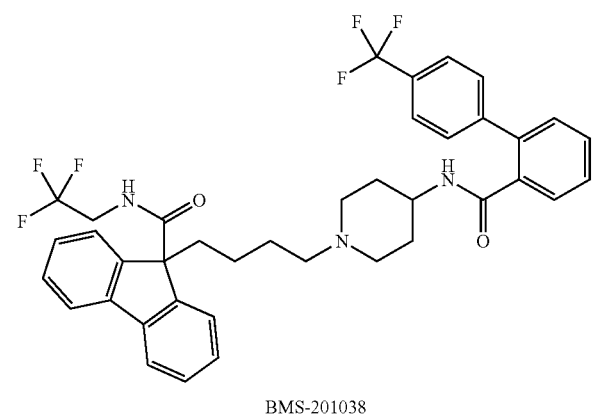
BMS-201038

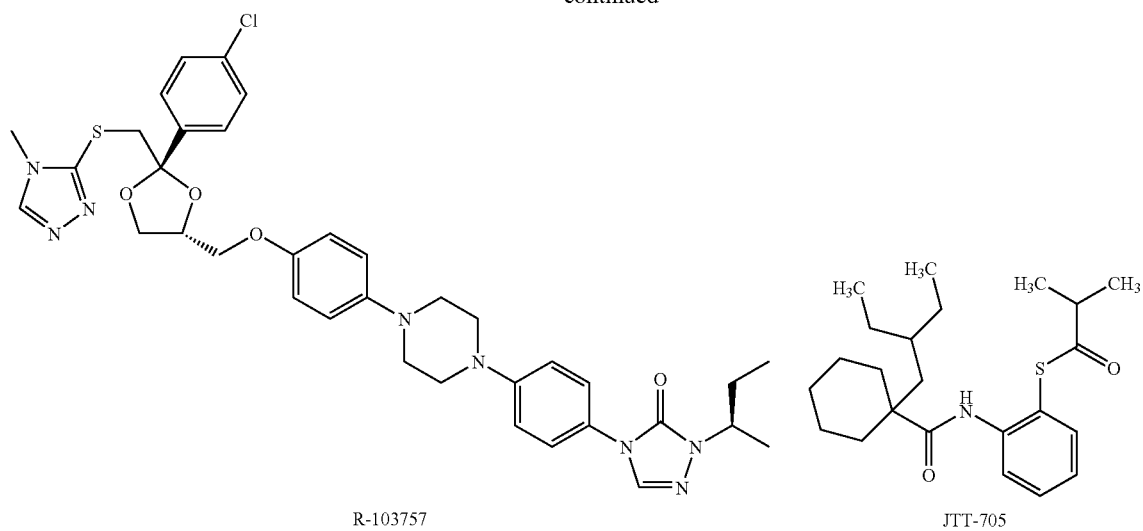
R-103757
JTT-705
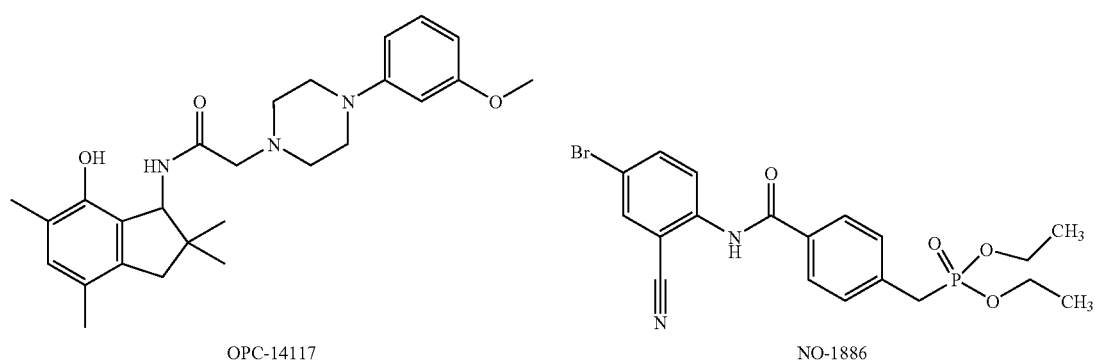
OPC-14117
NO-1886
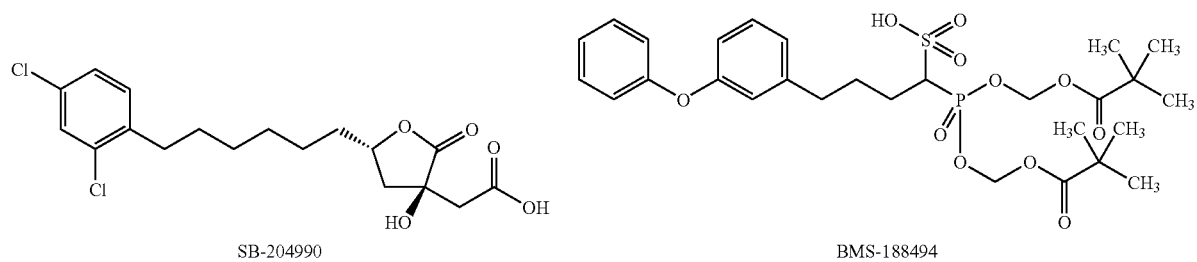
SB-204990
BMS-188494
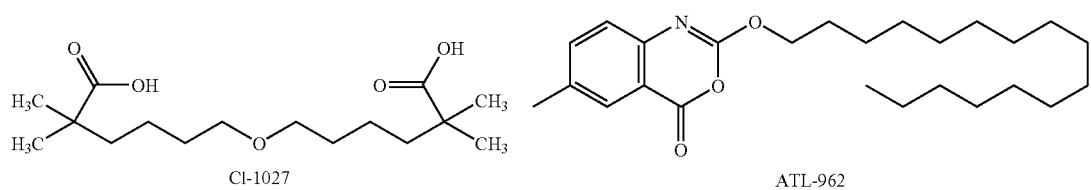
CI-1027
ATL-962

-continued
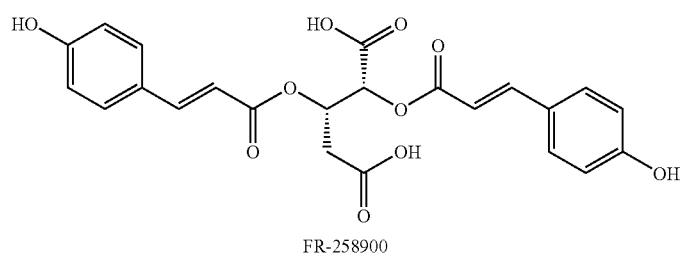
FR-258900
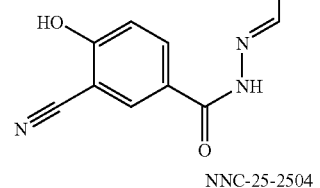
NNC-25-2504
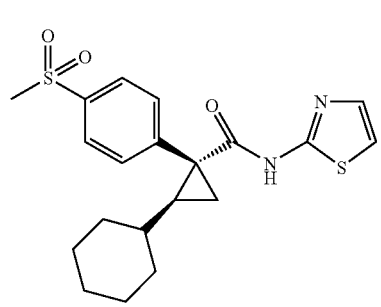
LY-2121260
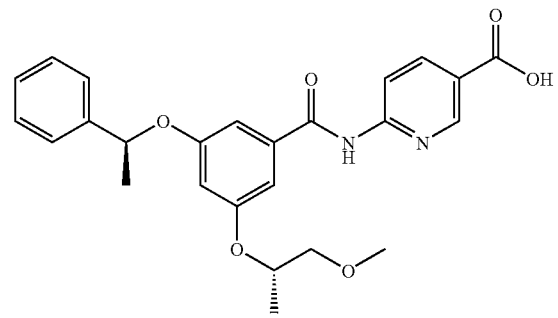
GKA-50
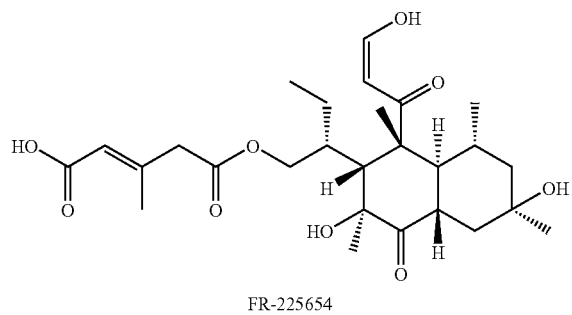
FR-225654
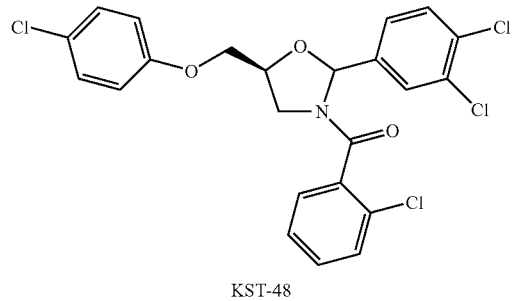
KST-48
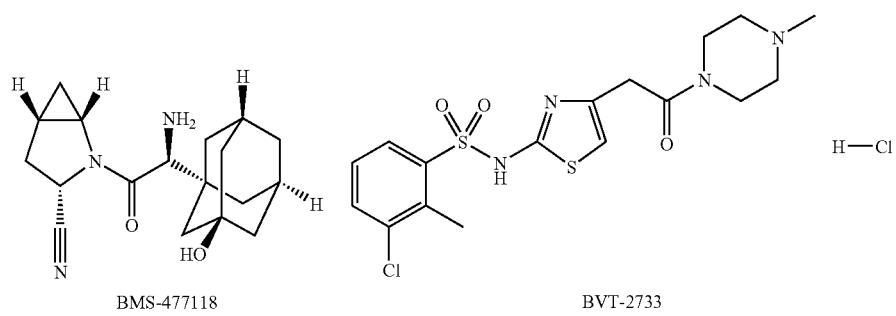
BMS-477118
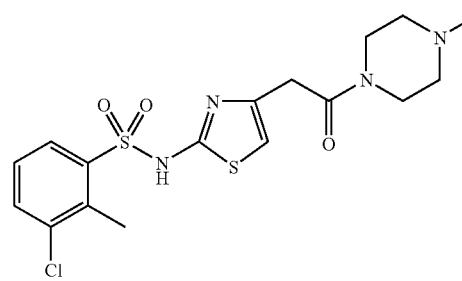
BVT-2733

-continued
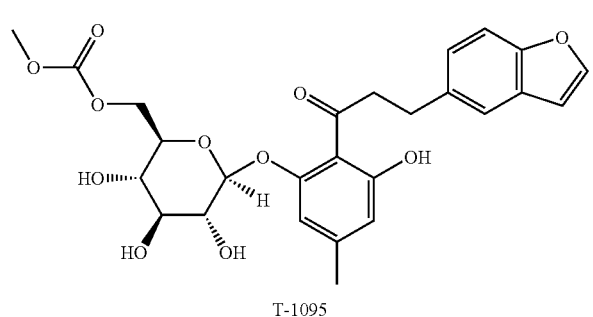
T-1095
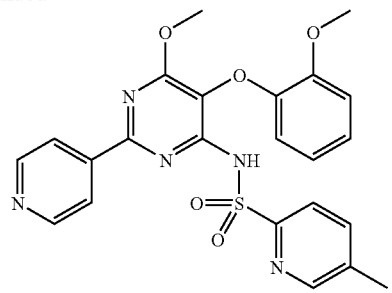
SPP-301
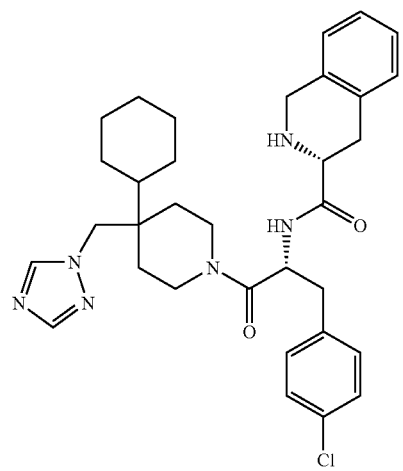
THIQ
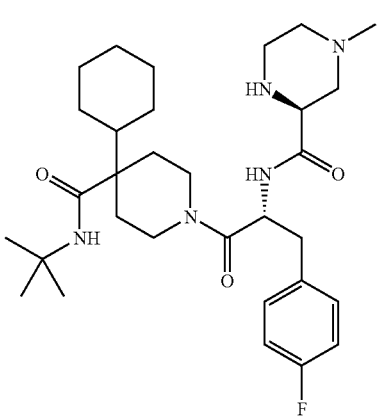
MB243
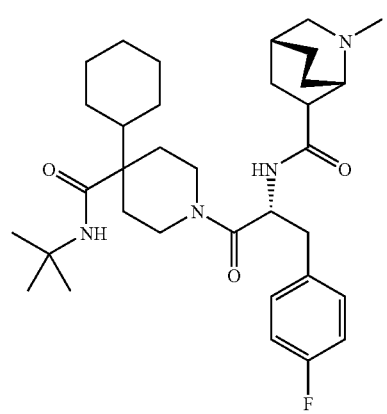
RY764
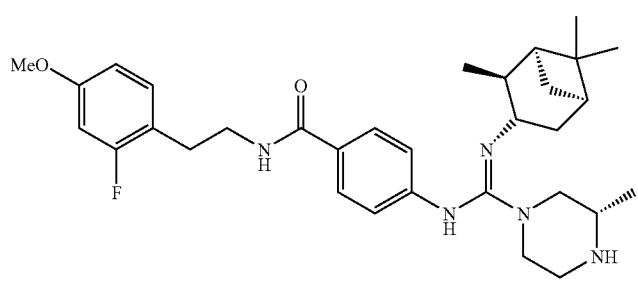
CHIR-785
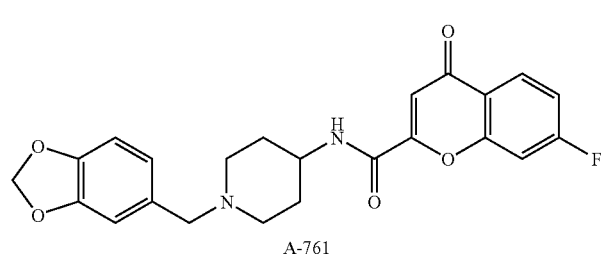
A-761
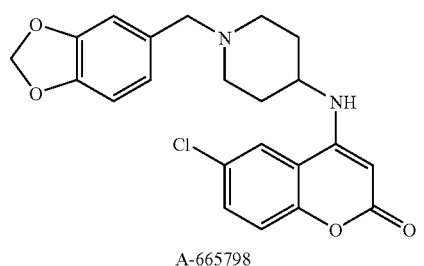
A-665798

-continued
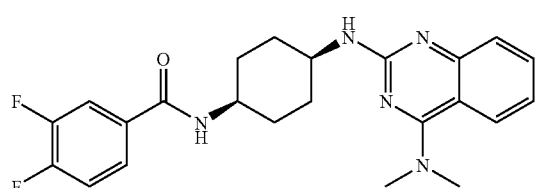
ATC-0175
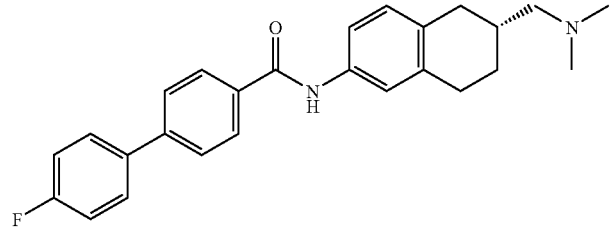
T-226296
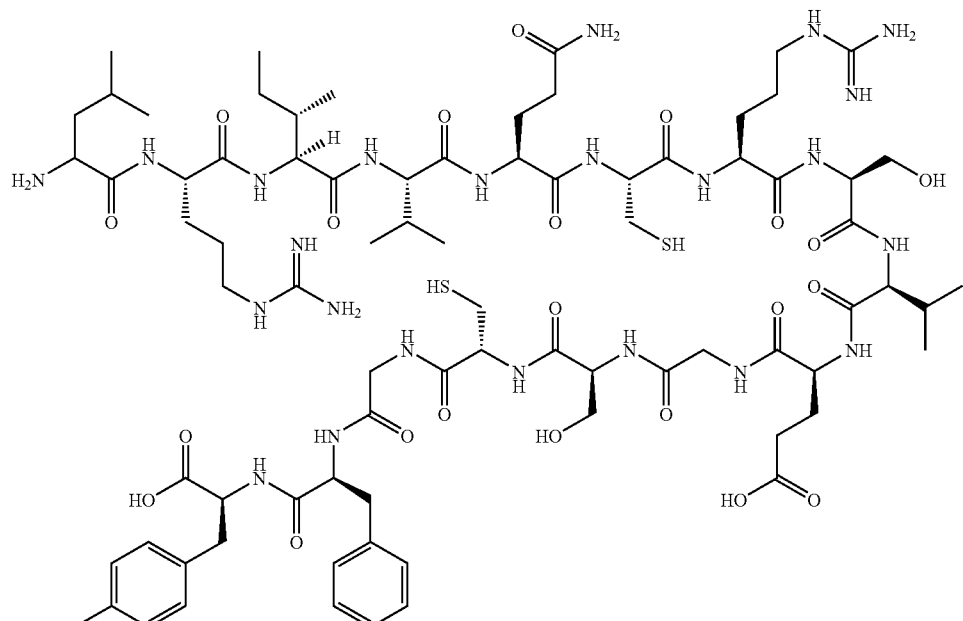
AOD-9604
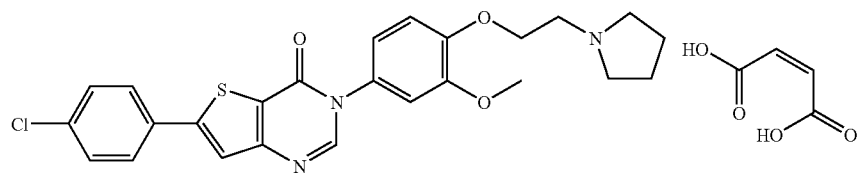
GW-803430
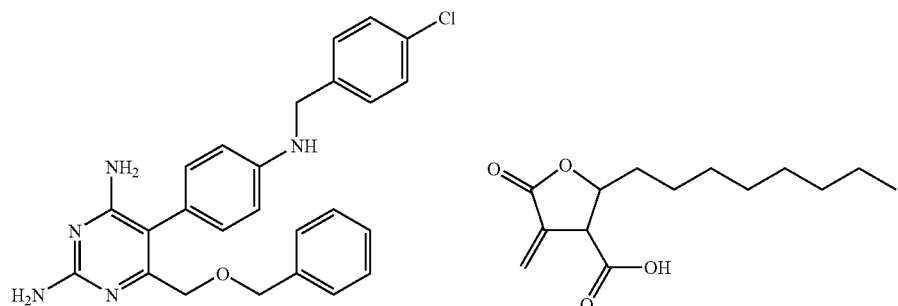
A-778193
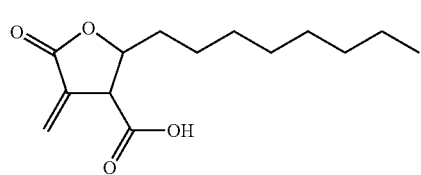
C75

-continued
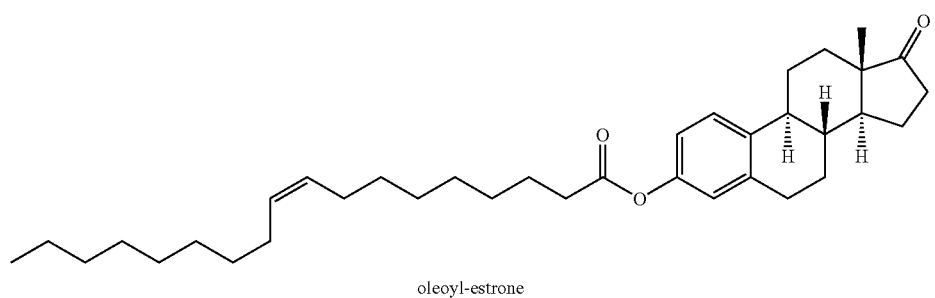
oleoyl-estrone
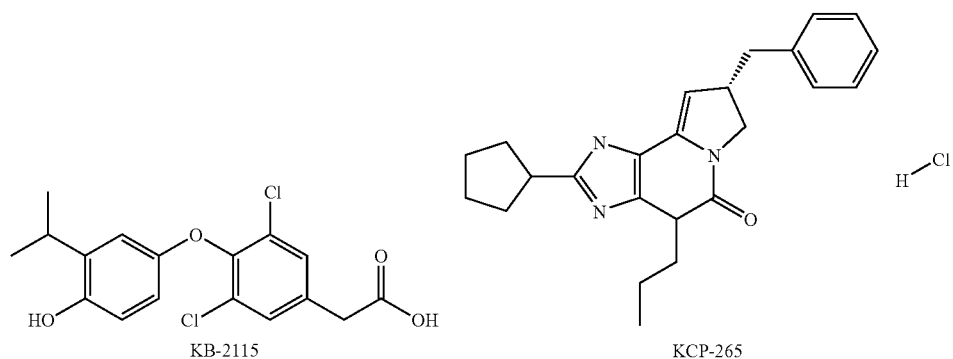
KB-2115    KCP-265
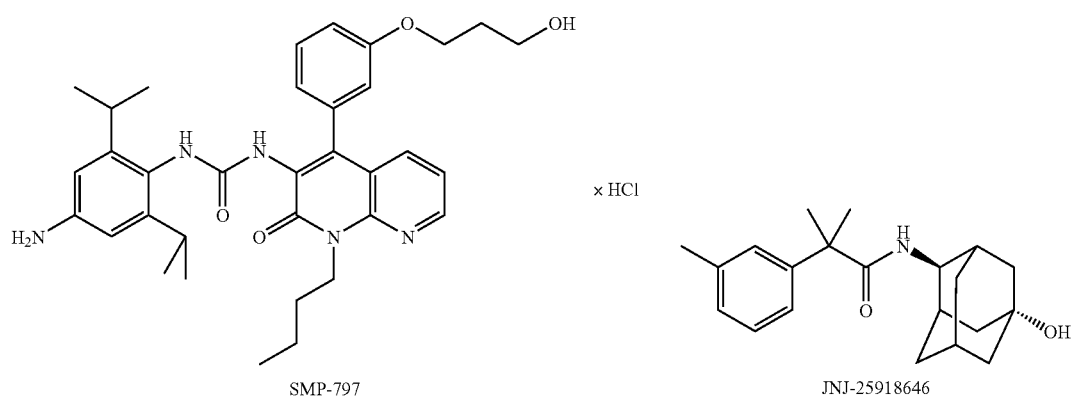
SMP-797    JNJ-25918646
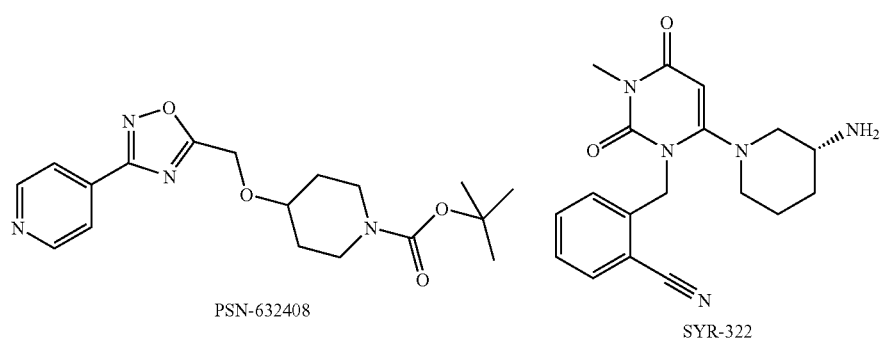
PSN-632408    SYR-322
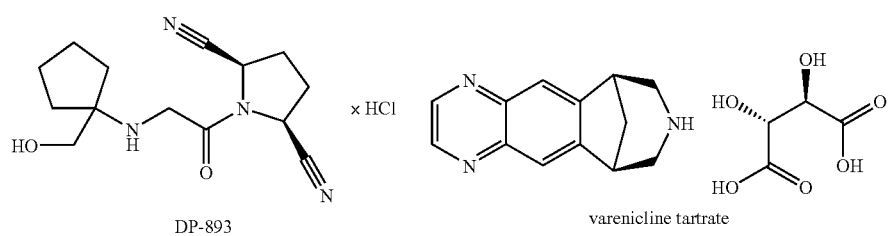
DP-893    varenicline tartrate -continued
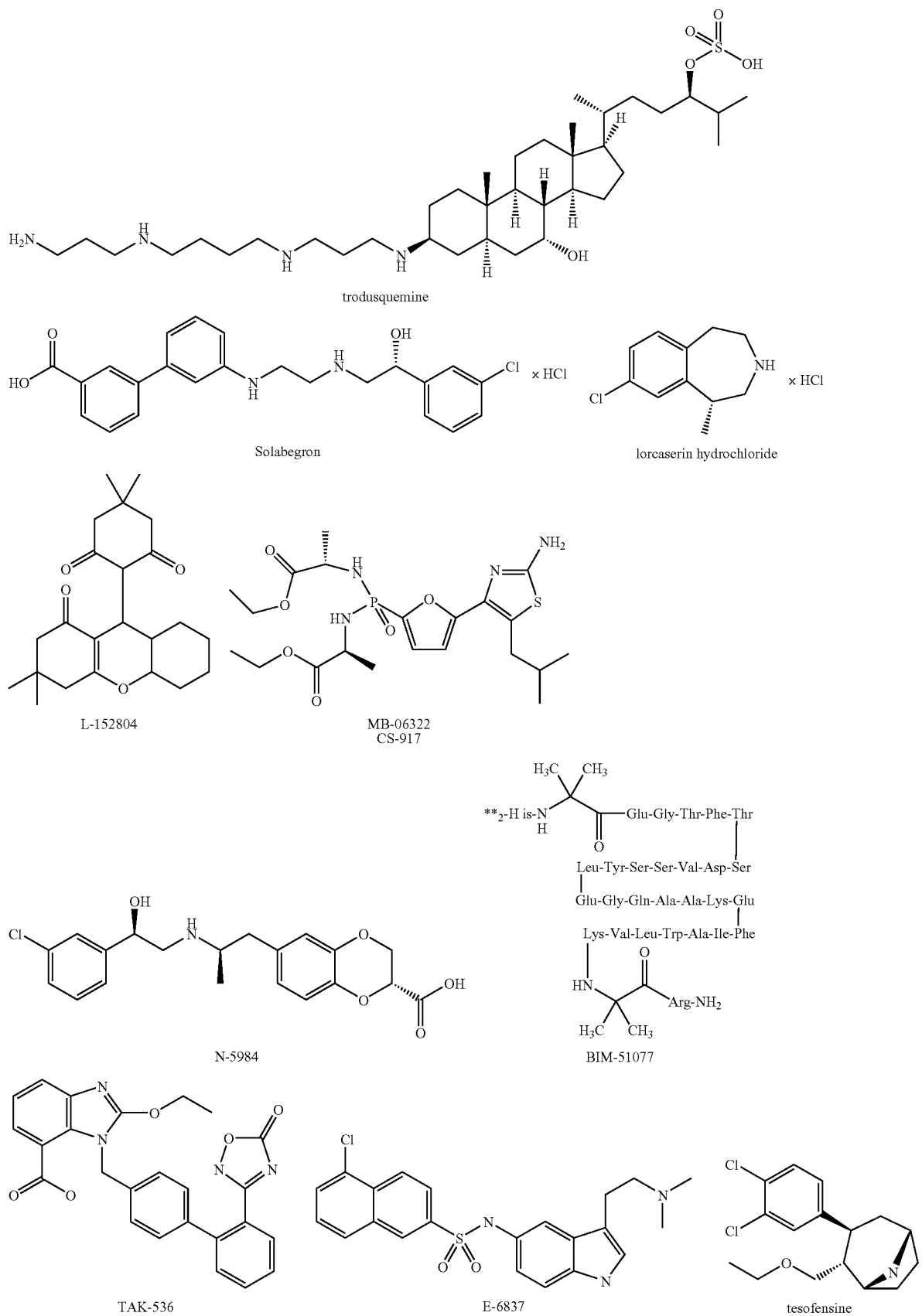

-continued
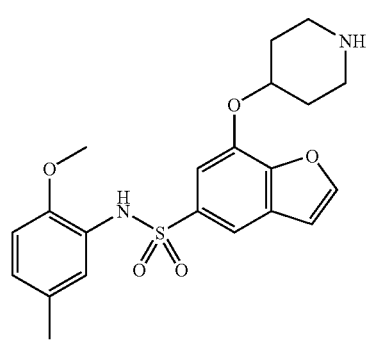
BVT-74316
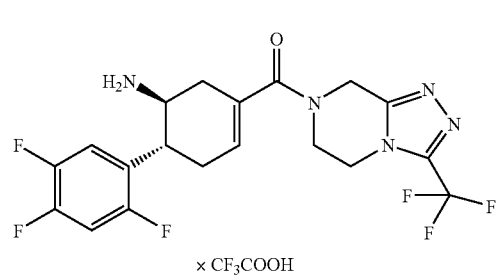
× CF₃COOH
ABT-341
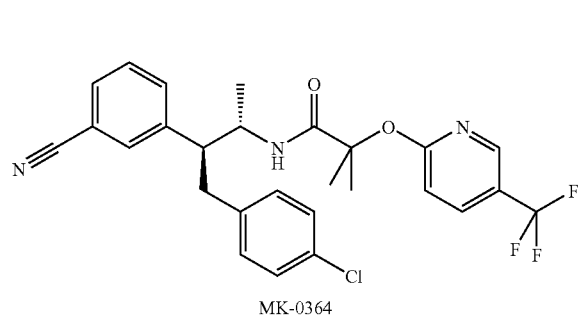
MK-0364
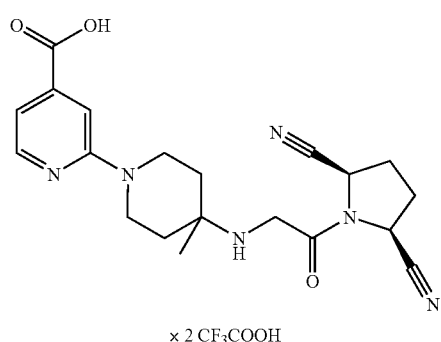
× 2 CF₃COOH
ABT-279
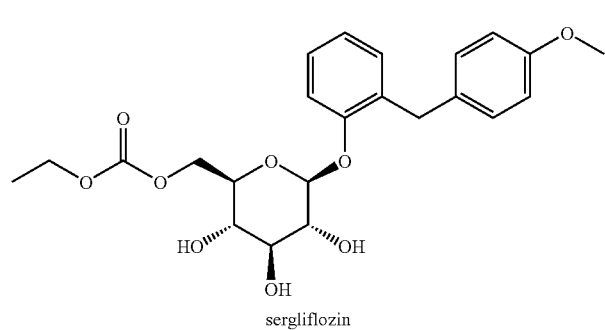
sergliflozin
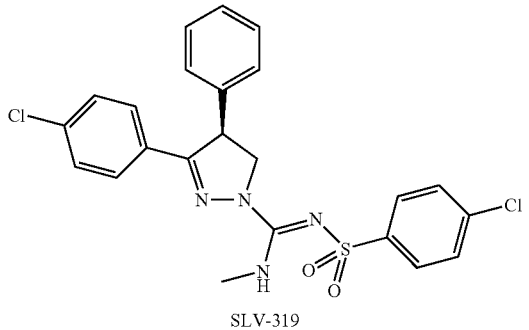
SLV-319
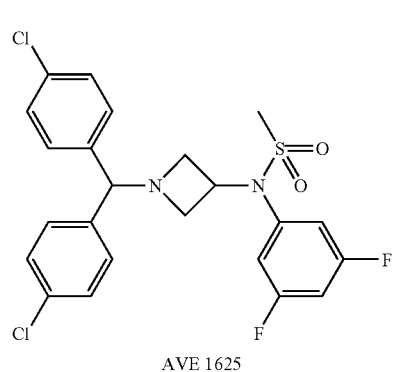
AVE 1625
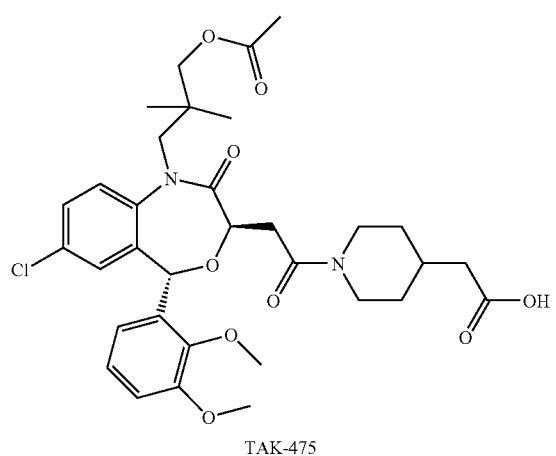
TAK-475

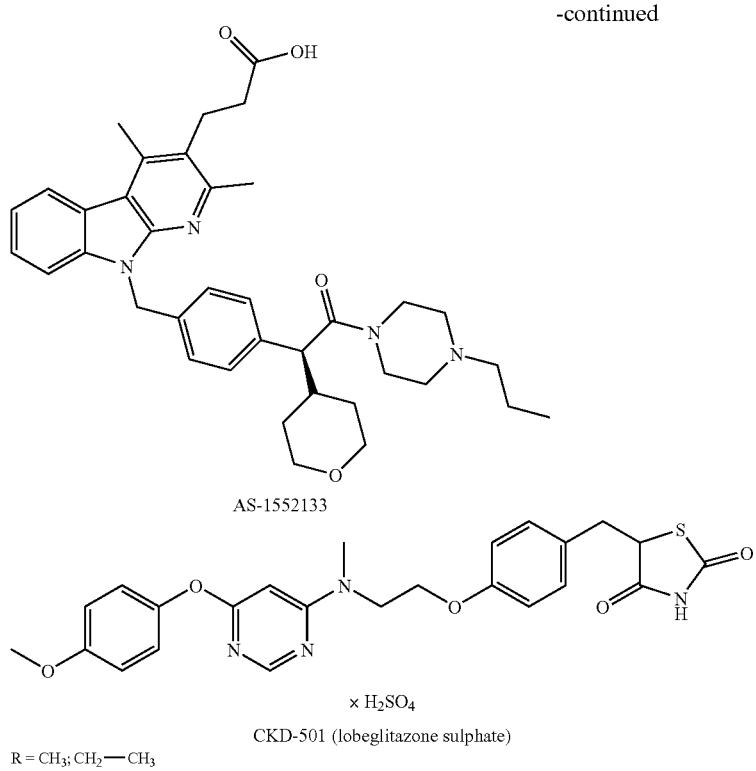

AS-1552133

CKD-501 (lobeglitazone sulphate)

R = CH₃; CH₂—CH₃

Also provided are processes for preparing the compound of the formula I.

Process A:

The compound of the formula II prepared according to U.S. Pat. No. 7,205,290 is purified by chromatography, for example on RP 18 silica gel using a solvent system of water, acetonitrile and trifluoroacetic acid, and then converted by treatment with water into the crystalline hydrate of the formula I.

Process B:

The compound of the formula II prepared according to U.S. Pat. No. 7,205,290 is dissolved in an organic solvent or a mixture of organic solvents. In some embodiments, the organic solvent used is ethanol. To increase the solubility, water may be added. This solution is added to a suspension of seed crystals in water. The seed crystals required can be prepared, for example, by process A. The water may also comprise a proportion of an organic solvent.

The water content of the hydrate after drying under reduced pressure at elevated temperatures may also be considerably less than the value of 2.2% calculated for a monohydrate (n=1). If the compound is exposed to ambient air (having, for example, a relative humidity of 40-60%), the water content quickly returns to a value close to the theoretical value.

Also provided are crystalline hydrates of the formula I prepared by a process described herein.

The invention is further illustrated by the following non-limiting examples.

The preparation of some examples is described in detail below, the other hydrates of the compound of the formula I were obtained analogously.

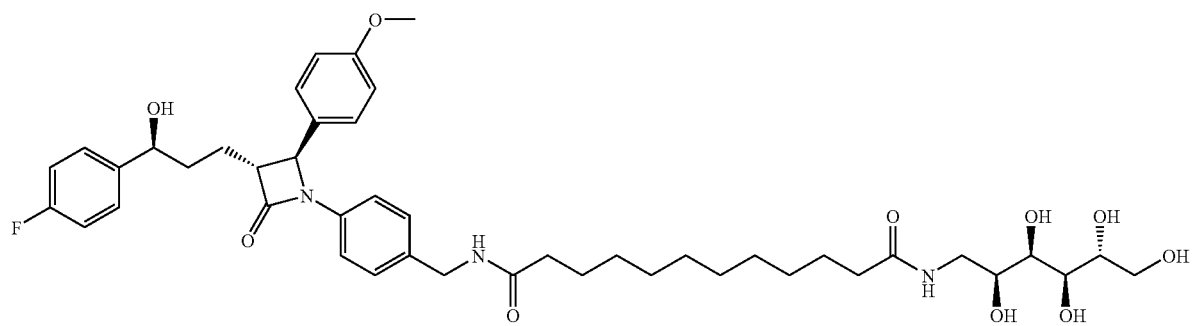

II

EXPERIMENTAL PART

Example 1

Figure 3:
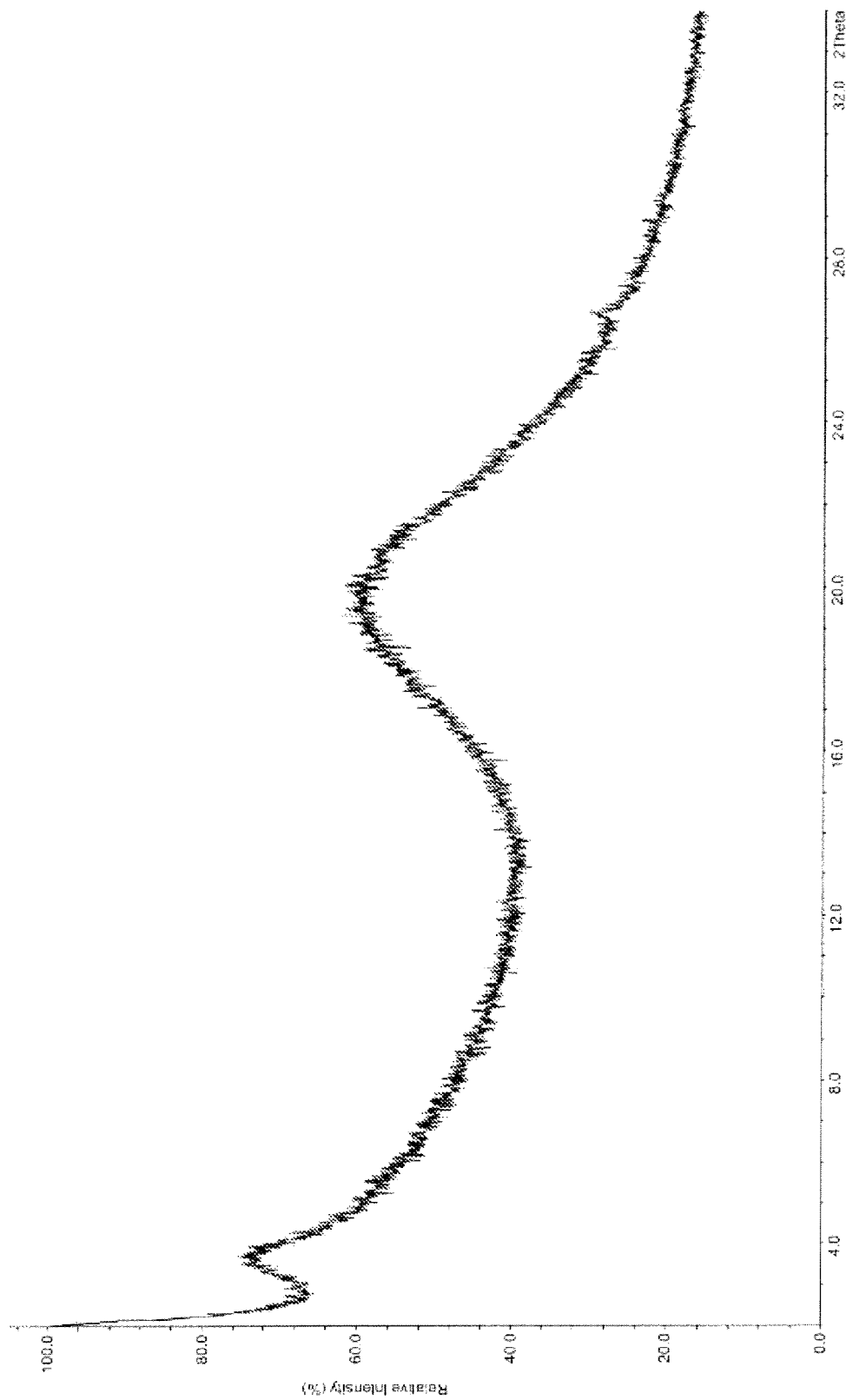
FIG. 3 shows the X-ray powder diffraction (XRPD) pattern of the amorphous product prepared in Example 1.

The amorphous compound of the formula II (purity according to HPLC: 95.8%, water content: 0.3%) is purified by chromatography:
Stationary phase: Kromasil C-18, 7 μm
Column volume: 1.7 L
Column length: 22 cm
Mobiles phases:
  A: water/acetonitrile=9/1 (vol/vol) with 0.1% by volume of trifluoroacetic acid added
  B: water/acetonitrile=1/9 (vol/vol) with 0.1% by volume of trifluoroacetic acid added
Flow rate: 200 ml/min
Gradient:
  t=0 min; 20% of mobile phase B
  t=90 min, 47% of mobile phase B
Application of substance: 8 g of compound II are dissolved in 770 ml of mobile phase B and diluted with 3500 ml of mobile phase A. The solution is filtered and applied to the column using a flow rate of 200 ml/min. The substance is then eluted using the above gradient. Fractions having a purity of >99% are combined. The acetonitrile is distilled off on a rotary evaporator at a bath temperature of <40° C., and the residue is freeze-dried. From 80 g, it was possible to obtain 60 g of the compound of the formula II having a purity according to HPLC of >99%. The amorphous product contained 0.38% of water and 3.1% of trifluoroacetic acid. The XRPD of this amorphous product of formula II exhibits the XRPD shown in FIG. 3.

58 g of the compound of the formula II having a purity according to HPLC of >99% in 1 L of 2% strength sodium bicarbonate solution were stirred at 20-25° C. for one hour and then in an ice bath for 30 minutes. The product is filtered off and triturated twice in total as described above with 1 L of water. The product is then dried under reduced pressure at 50° C. This gives 55.5 g of the crystalline compound of the formula I having a water content of 1.9%, which corresponds to n=0.86. Owing to natural deviations in the samples or in the measuring method (according to Karl Fischer), the values for the water content can be stated with an accuracy of +/−0.1%.

The compound of the formula I obtained exhibits the XRPD shown in FIG. 1. Exemplary 2 theta values are summarized in table 1.

TABLE 1

| 2 theta (+/−0.2 degrees 2 theta) |
| --- |
| 4.39 |
| 7.33 |
| 8.92 |
| 10.69 |
| 12.19 |
| 12.59 |
| 13.38 |
| 14.31 |
| 15.83 |
| 16.05 |
| 16.59 |
| 17.31 |
| 17.68 |
| 18.39 |
| 18.83 |
| 19.52 |
| 20.03 |
| 20.43 |
| 20.83 |
| 21.58 |
| 22.30 |
| 23.26 |
| 24.06 |
| 24.55 |
| 25.37 |
| 26.65 |
| 27.79 |
| 28.41 |
| 29.17 |
| 30.04 |
| 30.56 |
| 31.37 |
| 31.90 |
| 32.39 |
| 33.10 |

Owing to natural deviations in the samples or in the measuring method, the 2 theta values of the peaks can be stated with an accuracy of +/−0.2 degrees theta. However, it is common to see some measurement variations in reported data due to, for example, instrumental variations and environmental disturbances, such as preferred orientation, sample surface and inter-apparatus variability, and thus even the same forms of a compound may not exhibit the same exact XRPD data (in terms of D-spacing and peak intensity) all the time. Thus, even when the specific numerical values are not identical in every measurement, if the overall pattern is reproduced and the peak locations and relative peak intensities are sufficiently similar, one of skill in the art, using known and accepted techniques for such evaluation, can conclude that all of the obtained data demonstrate a single crystalline form.

Example 2

100 g of the amorphous compound II (purity according to HPLC: 95.8%, water content: 0.3%) are dissolved in 400 ml aqueous ethanol (denatured with methyl ethyl ketone, 80% (vol/vol)) by heating to 40° C. The solution is allowed to cool to 20-25° C. At 20-25° C., 2 g of the crystalline compound I from Example 1 are suspended by stirring in 10 L of distilled water. Over a period of 70 minutes, the solution of compound II in 80% of ethanol is added to this suspension. The vessel from which the solution was added is then rinsed with another 40 ml of 80% ethanol. A white precipitate is formed. The mixture is then stirred at 20-25° C. for another 20 h. The precipitate is filtered off with suction and washed a little at a time with a total of 5 L of distilled water. After drying at 40° C. under reduced pressure, 88.3 g of the crystalline hydrate of the formula I are obtained (water content: 2.9%, which corresponds to n=1.3).

Figure 2:
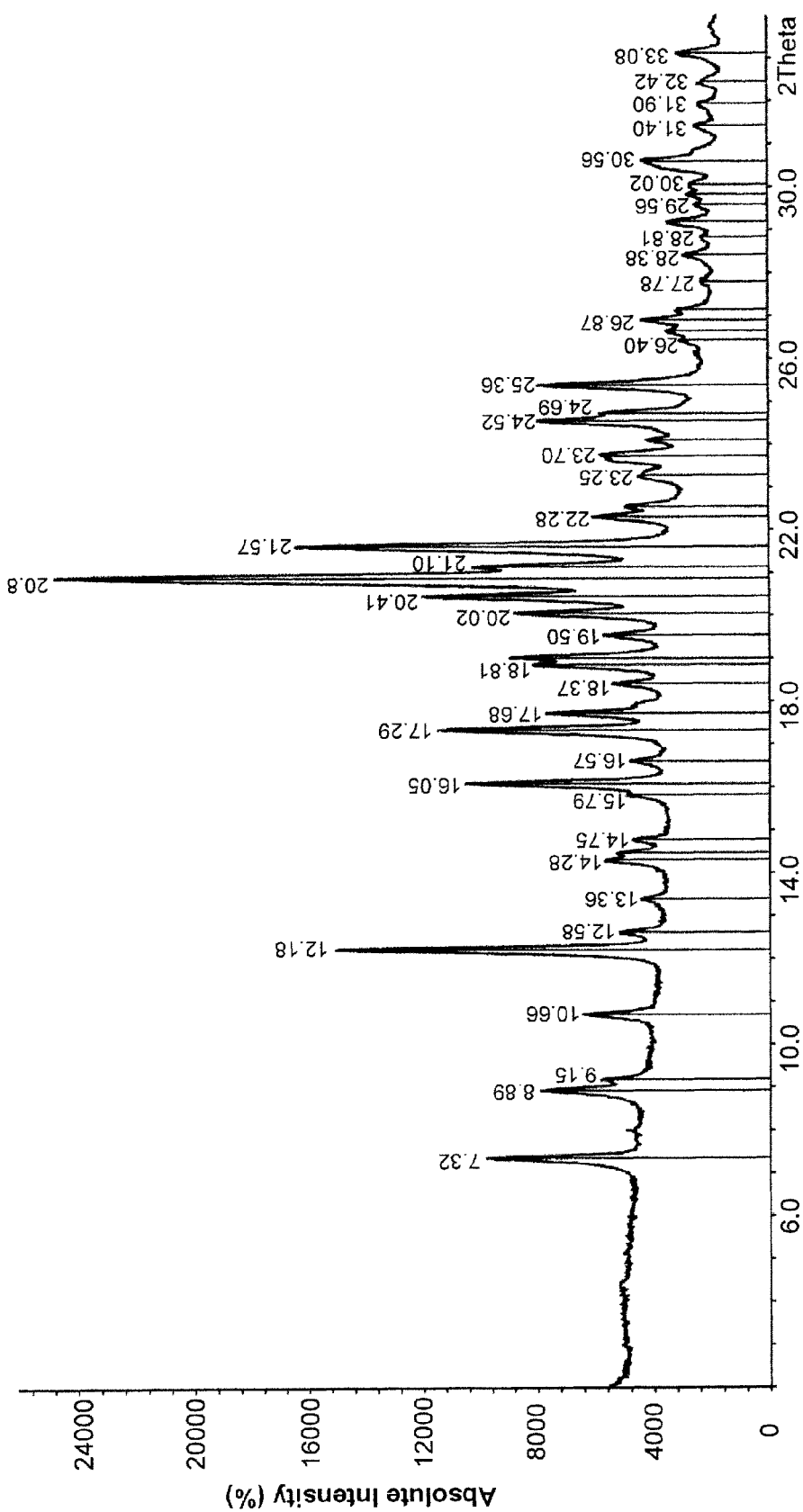
FIG. 2 shows the X-ray powder diffraction (XRPD) pattern of the crystalline hydrate of formula I prepared by Example 2.

The compound of the formula I obtained exhibits the XRPD shown in FIG. 2. Exemplary 2 theta values are summarized in table 2.

TABLE 2

| 2 theta (+/−0.2 degrees 2 theta) |
| --- |
| 7.32 |
| 8.89 |
| 9.15 |
| 10.66 |
| 12.18 |
| 12.58 |
| 13.36 |
| 14.28 |

TABLE 2-continued

| 2 theta (+/−0.2 degrees 2 theta) |
|---|
| 14.75 |
| 15.79 |
| 16.05 |
| 16.57 |
| 17.29 |
| 17.68 |
| 18.37 |
| 18.81 |
| 19.50 |
| 20.02 |
| 20.41 |
| 20.8 |
| 21.10 |
| 21.57 |
| 22.28 |
| 23.25 |
| 23.70 |
| 24.52 |
| 24.69 |
| 25.36 |
| 26.40 |
| 26.87 |
| 27.78 |
| 28.38 |
| 28.81 |
| 29.56 |
| 30.02 |
| 30.56 |
| 31.40 |
| 31.90 |
| 32.42 |
| 33.08 |

Example 3

25 g of the amorphous compound II (purity according to HPLC: 95.8%, water content: 0.3%) are dissolved in 100 ml aqueous ethanol (denatured with methyl ethyl ketone, 80% (vol/vol)) by heating to 40° C. The solution is allowed to cool to 20-25° C. At 20-25° C., 500 mg of the crystalline compound I from Example 1 are suspended by stirring in 500 ml of distilled water. Over a period of 60 minutes, the solution of compound II in 80% of ethanol is added to this suspension. The vessel from which the solution was added is then rinsed with another 10 ml of 80% ethanol. A white precipitate is formed. The mixture is then stirred at 20-25° C. for another 20 h. The precipitate is filtered off with suction and washed with distilled water. After drying at 45° C. under reduced pressure, 24.7 g of the crystalline hydrate are obtained. The XRPD confirms that the crystalline hydrate of Formula I was obtained.

Example 4

10 g of the amorphous compound II (purity according to HPLC: 95.8%, water content: 0.3%) are dissolved in 40 ml aqueous ethanol (denatured with methyl ethyl ketone, 80% (vol/vol)) by heating to 40° C. The solution is allowed to cool to 20-25° C. At 20-25° C., 0.2 g of the crystalline compound of the formula I from Example 1 is suspended by stirring in 1000 ml of distilled water. Over a period of 10 minutes, the solution of compound II in 80% of ethanol is added to this suspension. A white precipitate is formed, which is filtered off with suction and resuspended by stirring in 1 L of water. The mixture is then stirred at 20-25° C. for another 1 h. The precipitate is filtered off with suction and washed with 20 ml of distilled water. After drying at 50° C. under reduced pressure, 7.87 9 of the crystalline hydrate of the formula I are obtained. The XRPD confirms that the crystalline hydrate of Formula I was obtained.

Example 5

In 35.3 g of ethanol (denatured with methyl ethyl ketone) and 9.75 g of distilled water, 12 g of the amorphous compound II (purity according to HPLC: 97.1%) are heated to the boil. 2.3 g of liquid are distilled off. The solution is allowed to cool to 20-25° C. At 20-25° C., 0.12 g of the crystalline compound of the formula I is suspended by stirring in 414 ml of distilled water. Over a period of 45 minutes, the solution of compound II in ethanol/water is added to this suspension. The vessel from which the solution was added is rinsed with a mixture of 9.75 g of ethanol and 2.25 g of water.

The mixture is then stirred for another 18 h. The precipitate is filtered off with suction and washed with 60 ml of distilled water. After drying at 40° C. under reduced pressure, 11.7 g of the crystalline hydrate of the formula I (water content: 2.3%, which corresponds to n=1.05) are obtained. The XRPD confirms that the crystalline hydrate of Formula I was obtained.

Example 6

The hydrate obtained in Example 2 was dried under reduced pressure at 50° C. until a water content of 0.8% had been reached. The crystalline product was stored at 23° C./60% relative atmospheric humidity.

| Storage time (h) | Water content (%) | n |
|---|---|---|
| 0.5 | 1.1 | 0.5 |
| 2 | 2.4 | 1.09 |
| 4 | 2.5 | 1.14 |
| 6 | 2.4 | 1.09 |
| 24 | 2.5 | 1.14 |

The XRPD after 24 hours confirms that the crystalline hydrate of Formula I was obtained.

Test of Pharmacological Activity:

Using the method described below, the crystalline hydrate of formula I was examined for its activity:

Effect on Cholesterol Absorption+$^3$H-Taurocholic Acid Elimination via Fecal Elimination in Mice, Rats or Hamsters NMRI mice, Wistar rats or Golden Syrian hamsters (in groups of n=4-6) are kept with a standard diet (Altromin, Lage (Lippe), Germany) in metabolic cages. The afternoon prior to the administration of the radioactive tracers ($^{14}$C-cholesterol) the feed is withdrawn, and the animals are adapted to the cage wires.

In addition, 24 hours prior to the peroral administration of the test meal ($^{14}$C-cholesterol in Intralipid® 20, Pharmacia-Upjohn), the animals are labelled s.c. with $^3$H-TCA (taurocholic acid) (for example 1 μCi/mouse to 5 μCi/rat).

Cholesterol absorption test: 0.25 ml/mouse Intralipid® 20 (Pharmacia-Upjohn) (spiked with 0.25 μCi $^{14}$C-cholesterol in 0.1 mg of cholesterol) is administered perorally using a stomach tube.

Test substances are prepared separately in 0.5% methylcellulose (Sigma)/5% Solutol (BASF, Ludwigshafen, Germany) or in a suitable vehicle.

The application volume of the test substance is 0.5 ml/mouse. The test substance is administered immediately prior to the test meal (Intralipid with $^{14}$C-cholesterol label) (cholesterol absorption test).

The feces are collected over a period of 24 h: the fecal elimination of $^{14}$C-cholesterol and 3H-taurocholic acid (TCA) is determined after 24 hours.

The livers are removed and homogenized, and aliquots are incinerated in an Oximate (Model 307, Packard) to determine the amount of $^{14}$C-cholesterol taken up/resorbed.

Evaluation:

Feces Samples:

The total weight is determined, the sample is made up with water to a defined volume and then homogenized, an aliquot is evaporated to dryness and incinerated in an Oximate (Model 307, Packard, for the incineration of radioactively labelled samples): the amount of radioactive $^{3}$H—H$_2$O und $^{14}$C—CO$_2$ is extrapolated to the amount of $^{3}$H-taurocholic acid or $^{14}$C-cholesterol eliminated (dual isotope technique). The ED$_{200}$ values are interpolated as a dose from a dose-activity curve as the doses which double the elimination of TCA or cholesterol, based on a control group treated simultaneously.

Liver Samples:

The amount of $^{14}$C-cholesterol taken up into the liver is referenced to the dose administered. The ED$_{50}$ values are interpolated from a dose-activity curve as the dose which halves the uptake of $^{14}$C-cholesterol into the liver (50%), based on a control group.

Example No. 2 exhibits an ED$_{200}$ value (fecal elimination [mg/mouse]) of 0.01 mg/mouse)

The measured ED$_{200}$ value confirms the activity of the compounds of the formula I described herein and demonstrates that the crystalline hydrates of the formula I have very good cholesterol absorption-inhibiting activity.

Test of the Dissolution Rate:

The dissolution rate of the crystalline hydrates of the formula I was tested as follows:

The dissolution rate is measured in a standard apparatus (paddle) according to the US Pharmacopeia (USP 27) at 37° C. The stirrer speed is 75 rpm.

20 mg of the substance to be examined are added to 1000 ml of a 0.1% strength aqueous sodium dodecylsulfate (SDS) solution. After 15, 30, 45 and 60 minutes, samples of 20 ml are taken.

The portion dissolved is determined photometrically at 256 nm using a comparison solution. The measurement is carried out in 10 mm cuvettes using, for example, a Perkin Elmer Lambda 25 photometer. The samples are measured directly after removal of the samples. In each case, a mean is calculated from three determinations.

The comparison solution is prepared as follows: 2-3 mg of the batch used are dissolved in 2 ml of dimethylformamide in a measuring flask. The volume is then made up to 100.0 ml using 0.1% strength SDS solution.

The amorphous compound of the formula I used in Example 2 was compared to the crystalline compound of the formula I obtained in the same Example 2. The results are compiled in the table below:

| Time [min] | Amorphous compound of the formula II (release [%]) | Crystalline compound of the formula I (release [%]) |
|---|---|---|
| 15 | 30.0 | 88.0 |
| 30 | 41.3 | 90.0 |
| 45 | 44.7 | 94.6 |
| 60 | 46.2 | 98.7 |

Compared to the amorphous compound of the formula II from U.S. Pat. No. 7,205,290, the crystalline hydrates of the formula I have a considerably increased dissolution rate.

Accordingly, provided are crystalline hydrates of the formula I wherein, after 15 minutes at least 50% of the crystalline hydrate of the formula I is dissolved when the dissolution rate of 20 mg of the crystalline hydrate of the formula I in 1000 ml of a 0.1% strength aqueous sodium dodecylsulfate solution is measured in a standard paddle apparatus according to the USP 27 at 37° C. and a stirrer speed of 75 rpm.

In some embodiments, after 15 minutes at least 70% of the crystalline hydrate of the formula I are in solution.

In some embodiments, after 15 minutes at least 85% of the crystalline hydrate of the formula I are in solution.

For active ingredients to be able to display their activity in the body, they may be present, at least in part, in dissolved form at the site of action. Here, solubility and dissolution rate in aqueous environments are two important factors. There is virtually no difference between the solubilities of amorphous and crystalline compounds as the solubility is a thermodynamic quantity. This is different for the dissolution rate, since it is a kinetic quantity. In general, crystalline compounds have, compared to amorphous compounds, a lower dissolution rate since the crystalline compounds are thermodynamically more stable.

It is therefore an advantage that the crystalline hydrate of the formula I has a considerably higher dissolution rate compared to the amorphous compound II. After only 15 minutes, a large part of the active ingredient is already in solution. This is almost three times the amount of the amorphous active ingredient. Thus, the onset of the action of the crystalline hydrate of the formula I will be faster than the onset of the action of the amorphous compound of the formula II.

As those skilled in the art will appreciate, numerous changes and modifications may be made to the embodiments of the invention without departing from the spirit of the invention. It is intended that all such variations fall within the scope of the invention.

The invention claimed is:

1. At least one crystalline hydrate of the formula I,

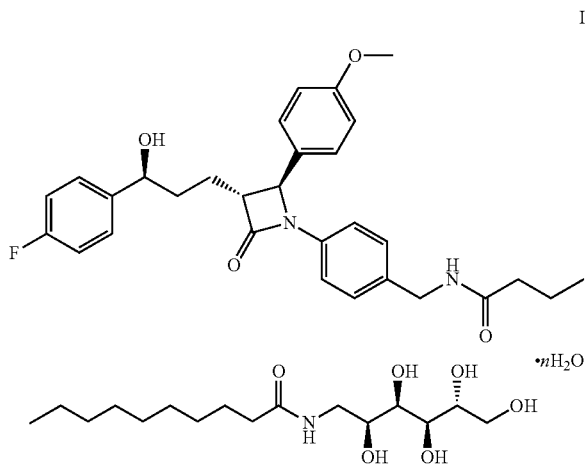

wherein n has a value of from 0.8 to 1.3.

2. The at least one crystalline hydrate of claim 1 wherein n has a value of 1.

3. The at least one crystalline hydrate of claim 1 wherein the XRPD, measured with CuKα radiation, has at least peaks of the following 2 theta values: 12.19, 17.31, 20.43, 20.83, and 21.58, each of the diffraction angles being ±0.2 degrees 2 theta.

4. The at least one crystalline hydrate of claim 1 wherein the XRPD, measured with CuKα radiation, has at least peaks of the following 2 theta values: 7.33, 8.92, 12.19, 16.05, 17.31, 17.68, 18.83, 20.43, 20.83, 21.58, 24.55, and 25.37, each of the diffraction angles being ±0.2 degrees 2 theta.

5. A pharmaceutical composition comprising a pharmaceutically acceptable carrier and a therapeutically effective amount of at least one crystalline hydrate of claim 1.

6. The pharmaceutical composition according to claim 5 further comprising at least one HMGCoA reductase inhibitor.

7. The pharmaceutical composition according to claim 6, wherein the HMGCoA reductase inhibitor is selected from simvastatin, fluvastatin, pravastatin, lovastatin, atorvastatin, cerivastatin, and rosuvastatin.

8. The pharmaceutical composition according to claim 7, wherein the HMGCoA reductase inhibitor is atorvastatin.

9. The pharmaceutical composition according to claim 8, wherein the pharmaceutical composition comprises 1-50 mg of atorvastatin and 10-50 mg of the at least one crystalline hydrate of the formula I,

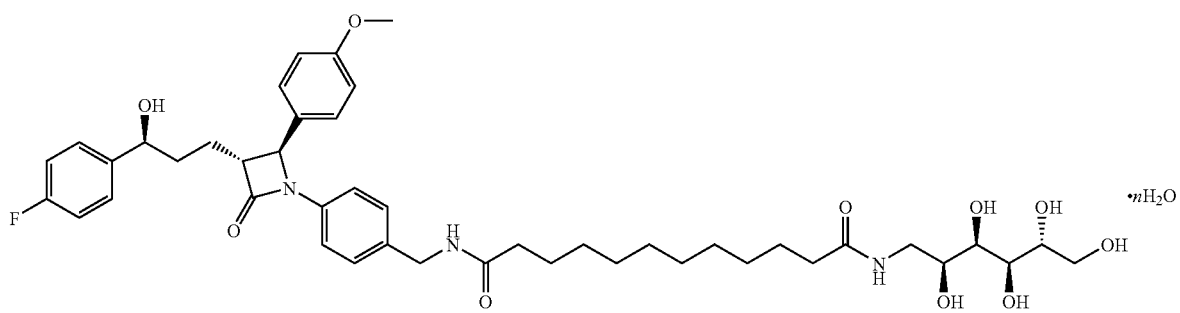

I wherein n has a value of from 0.8 to 1.3.

10. The pharmaceutical composition according to claim 9, wherein the pharmaceutical composition comprises 5-15 mg of atorvastatin and 15-50 mg of the at least one crystalline hydrate of the formula I.

11. The pharmaceutical composition according to claim 10, wherein the pharmaceutical composition comprises 10 mg of atorvastatin and 25 mg of the at least one crystalline hydrate of the formula I.

12. The pharmaceutical composition according to claim 10, wherein the pharmaceutical composition comprises 10 mg of atorvastatin and 50 mg of the at least one crystalline hydrate of the formula I.

13. A method of treating a mammal having hyperlipidemia comprising administering at least one crystalline hydrate of claim 1 to said mammal.

14. A method of treating a mammal having hyperlipidemia comprising
   formulating at least one crystalline hydrate of claim 1 with one or more pharmaceutically acceptable diluents to form a composition and
   administering the composition to said mammal.

15. A method of lowering the serum cholesterol level of a mammal comprising administering at least one crystalline hydrate of claim 1 to said mammal.

16. A method of lowering the serum cholesterol level of a mammal comprising
   formulating at least one crystalline hydrate of claim 1 with one or more pharmaceutically acceptable diluents to form a composition and
   administering the composition to said mammal.

* * * * *